United States Patent
Kühn et al.

(10) Patent No.: US 11,819,185 B2
(45) Date of Patent: Nov. 21, 2023

(54) FLEXIBLE ENDOSCOPE WITH SKELETON STRUCTURE

(71) Applicant: SCHÖLLY FIBEROPTIC GMBH, Denzlingen (DE)

(72) Inventors: Matthias Kühn, Freiburg (DE); Stefan Schröer, Freiburg (DE); Michael Schwärzle, Denzlingen (DE); Johannes Bourbon, Freiburg (DE); Lutz Labusch, Emmendingen (DE); Erwin Streck, Donaueschingen (DE); Holger Reinecke, Emmendingen (DE)

(73) Assignee: Scholly Fiberoptic GMBH, Denzlinger (DE)

( * ) Notice: Subject to any disclaimer, the term of this patent is extended or adjusted under 35 U.S.C. 154(b) by 0 days.

(21) Appl. No.: 17/237,332

(22) Filed: Apr. 22, 2021

(65) Prior Publication Data
US 2021/0330178 A1 Oct. 28, 2021

(30) Foreign Application Priority Data
Apr. 27, 2020 (DE) .......................... 102020111458.3

(51) Int. Cl.
*A61B 1/01* (2006.01)
*A61B 1/008* (2006.01)
*A61B 1/005* (2006.01)

(52) U.S. Cl.
CPC ................ *A61B 1/01* (2013.01); *A61B 1/008* (2013.01); *A61B 1/0057* (2013.01)

(58) Field of Classification Search
CPC .............. A61B 1/00096; A61B 1/0011; A61B 1/00135; A61B 1/005; A61B 1/0051;
(Continued)

(56) References Cited

U.S. PATENT DOCUMENTS

| 4,846,573 A | 7/1989 | Taylor et al. |
| 4,918,521 A | 4/1990 | Yabe et al. |

(Continued)

FOREIGN PATENT DOCUMENTS

| WO | 9713452 A1 | 4/1997 |
| WO | 2019002186 A1 | 1/2019 |

(Continued)

OTHER PUBLICATIONS

United States Office Action and list of Examiner cited references dated Feb. 14, 2023 from corresponding U.S. Appl. No. 17/237,280 (Year: 2023).*

(Continued)

*Primary Examiner* — Aaron B Fairchild
*Assistant Examiner* — Stephen Floyd London
(74) *Attorney, Agent, or Firm* — Grogan, Tuccillo & Vanderleeden, LLP

(57) ABSTRACT

A flexible endoscope for insertion into the human body includes a flexible section arranged in a distal end region of the endoscope. The endoscope further includes a tip segment distally adjoining the flexible section, the tip segment being controllable by at least one tension cord. A skeleton is formed in a flexible controllable section with guide elements that are movable relative to one another, each of which guides at least one tension cord laterally.

16 Claims, 16 Drawing Sheets

(58) Field of Classification Search
CPC ... A61B 1/0052; A61B 1/0053; A61B 1/0055;
A61B 1/0056; A61B 1/0057; A61B
1/008; A61B 1/018; A61B 1/051; A61B
1/053; A61B 1/0676; A61M 25/005;
A61M 25/0133; A61M 25/0138; A61M
25/0141; A61M 25/0144; A61M 25/0147;
A61M 25/0152; A61M 25/0155; A61M
25/0158; A61M 2025/015; A61M
2025/0161; A61M 2025/0163
USPC .................................................. 600/140, 141
See application file for complete search history.

(56) References Cited

U.S. PATENT DOCUMENTS

| | | | |
|---|---|---|---|
| 5,089,895 A | 2/1992 | Fraker et al. | |
| 6,364,828 B1* | 4/2002 | Yeung | A61B 1/0056 174/68.3 |
| 6,491,626 B1* | 12/2002 | Stone | F16D 1/00 403/291 |
| 2006/0167340 A1 | 7/2006 | Pease et al. | |
| 2007/0129466 A1 | 6/2007 | Kagawa et al. | |
| 2008/0287741 A1* | 11/2008 | Ostrovsky | A61B 1/008 600/141 |
| 2009/0093679 A1* | 4/2009 | Suigetsu | A61B 1/00128 600/139 |
| 2009/0137875 A1* | 5/2009 | Kitagawa | A61B 1/0055 600/146 |
| 2009/0253963 A1* | 10/2009 | Suigetsu | A61B 1/0055 425/446 |
| 2010/0160735 A1* | 6/2010 | Bakos | A61B 17/3417 600/141 |
| 2010/0217082 A1* | 8/2010 | Ito | G02B 23/2476 600/121 |
| 2011/0106101 A1 | 5/2011 | Tortonese et al. | |
| 2011/0288372 A1 | 11/2011 | Petersen | |
| 2012/0071864 A1* | 3/2012 | Banju | A61B 1/0057 606/1 |
| 2012/0238805 A1* | 9/2012 | Iwasaka | A61B 1/0055 600/104 |
| 2012/0245418 A1* | 9/2012 | Boulais | A61B 1/0011 29/527.1 |
| 2013/0041223 A1 | 2/2013 | Kato | |
| 2013/0281779 A1 | 10/2013 | Robertson | |
| 2016/0235274 A1* | 8/2016 | Graham | A61B 1/0055 |
| 2016/0317220 A1* | 11/2016 | Guo | A61B 18/1492 |
| 2018/0289242 A1 | 10/2018 | Dai | |
| 2018/0303325 A1 | 10/2018 | Fujimori | |
| 2019/0175869 A1 | 6/2019 | Kirt et al. | |
| 2020/0100662 A1 | 4/2020 | Jensen et al. | |
| 2020/0113415 A1* | 4/2020 | Kristensen | B29C 45/0053 |
| 2020/0297193 A1 | 9/2020 | Takahashi et al. | |
| 2021/0038209 A1* | 2/2021 | Gruner | A61B 34/30 |
| 2021/0068642 A1 | 3/2021 | Sorensen et al. | |
| 2021/0228064 A1 | 7/2021 | Sorensen et al. | |

FOREIGN PATENT DOCUMENTS

| | | |
|---|---|---|
| WO | 2020070851 A1 | 4/2020 |
| WO | 2021219180 | 11/2021 |
| WO | WO-2021219180 A1 * | 11/2021 |

OTHER PUBLICATIONS

United States Office Action and list of Examiner cited references dated Feb. 14, 2023 from corresponding U.S. Appl. No. 17/237,332 (Year: 2023).*

United States Office Action and list of Examiner cited references dated Aug. 19, 2022 from corresponding U.S. Appl. No. 17/237,332 (Year: 2022).*

United States Office Action and list of Examiner cited references dated Aug. 12, 2022 from corresponding U.S. Appl. No. 17/237,280 (Year: 2022).*

Office Action and References cited issued for U.S. Appl. No. 17/237,332.

* cited by examiner

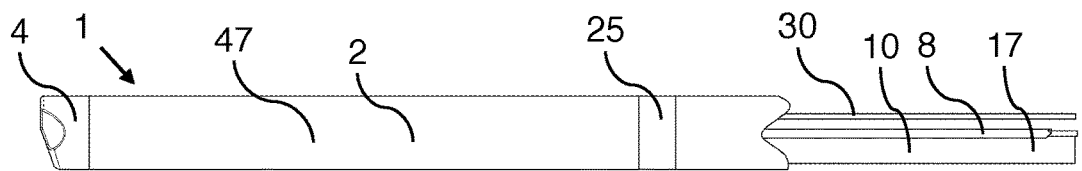
Fig. 10
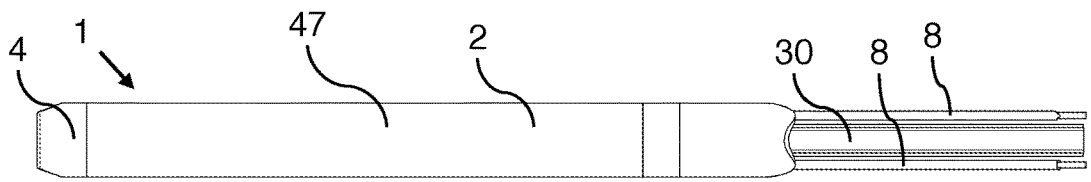
Fig. 11
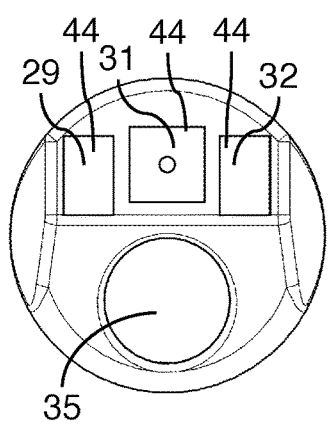 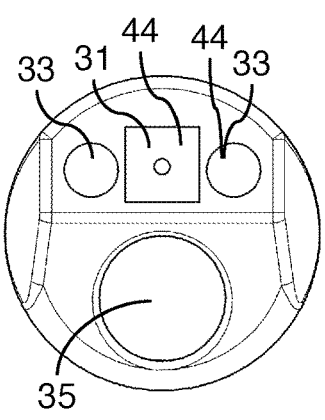 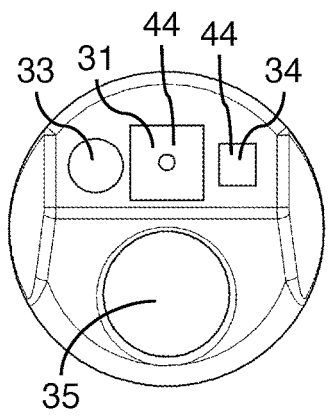
Fig. 12    Fig. 13    Fig. 14
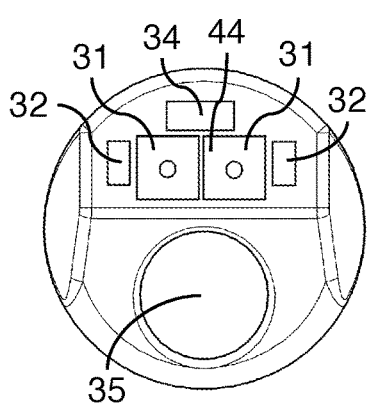 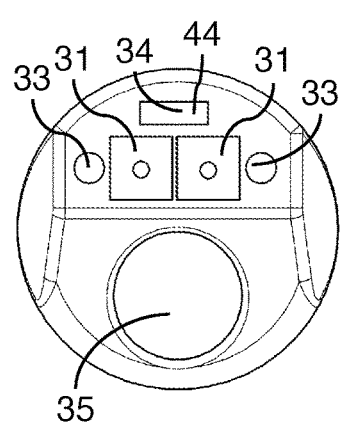 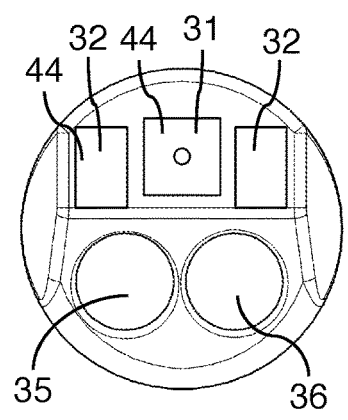
Fig. 15    Fig. 16    Fig. 17

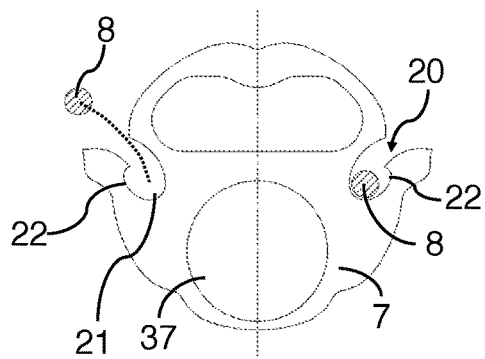
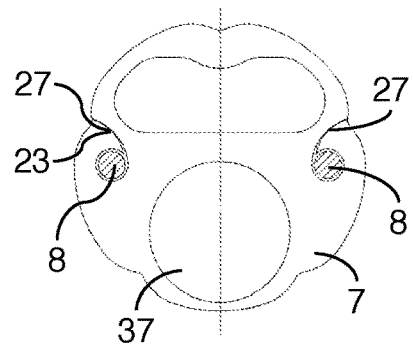
Fig. 32  Fig. 33
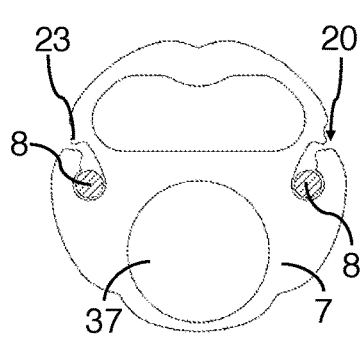
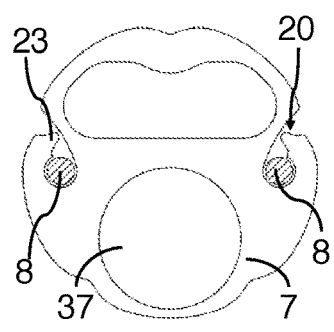
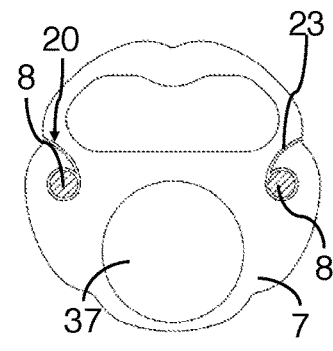
Fig. 34  Fig. 35  Fig. 36
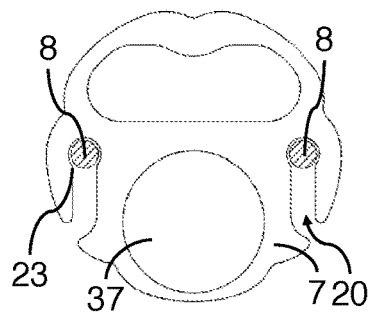
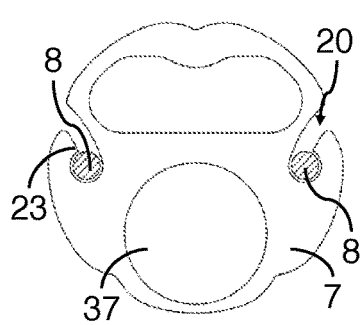
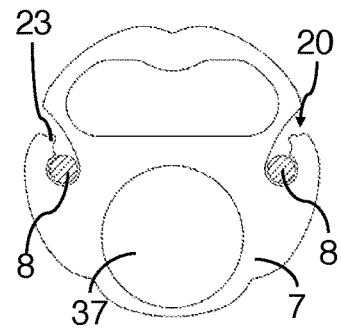
Fig. 37  Fig. 38  Fig. 39
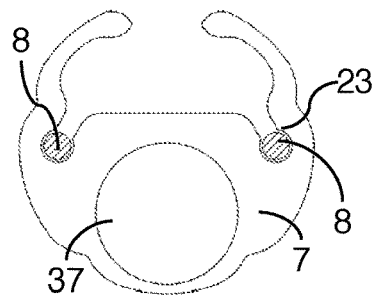
Fig. 40

FLEXIBLE ENDOSCOPE WITH SKELETON STRUCTURE

CROSS-REFERENCE TO RELATED APPLICATION

This application claims priority to German Patent Application No. 102020111458.3, filed on Apr. 27, 2020, which is herein incorporated by reference in its entirety.

FIELD OF THE INVENTION

The invention relates to a flexible endoscope with a flexible section, which is arranged in a distal end region of the endoscope, and with a tip segment distally adjoining the flexible section, said tip segment being controllable by means of at least one tension cord.

The invention further relates to a production or assembly method for such an endoscope.

BACKGROUND OF THE INVENTION

Endoscopes as described above are available on the market in many ways and are used in particular for medical interventions; that is to say, such endoscopes can in particular be designed in order to meet legal requirements so that they can be used for insertion into the human body.

There do currently exist very powerful endoscopes with controllable tip segments. However, these are very expensive to produce and are therefore only suitable for frequent reuse. For a wide variety of reasons, however, there is also a need for the endoscopes described above for single-use applications; that is to say, for applications in which the endoscope is only to be used once for a medical intervention and therefore, in particular, does not have to be sterilizable. In order to be able to produce such endoscopes at reasonable costs, which is essential if they are for single use, various approaches have been pursued. However, resorting to cheap elastomer materials often leads to inadequate performance of the endoscopes with regard to their mechanical properties; in particular, the controllability of such endoscopes suffers.

SUMMARY OF THE INVENTION

Proceeding from this background, the invention is based upon the problem of providing a flexible endoscope that can be produced easily and inexpensively, but at the same time has high mechanical stability, good reproducibility and controllability of the movement of the flexible section and thus of the tip segment of the endoscope. For simple production, a small number of built-in individual parts of the endoscope is also desired.

In order to solve this problem in a flexible endoscope, the features of claim 1 are provided according to the invention. In particular, according to the invention, in order to solve the problem in a flexible endoscope of the type mentioned above, it is proposed that the flexible section comprise a skeleton consisting of a large number of guide elements and that the at least one tension cord be guided by the guide elements. In this way, when the flexible section is sharply curved, the tension cord can be prevented or at least discouraged from escaping from the endoscope in that the guide elements absorb lateral forces. Such an escape of the tension cord carries the risk of tissue crushing or even tissue severance when, for example, the tension cord is oppositely stressed and seeks to re-enter the endoscope. A cutting of the tension cord into any investment composition that may be present can also be prevented or at least reduced. The useful life of the endoscope can thus be extended.

In this case, the guide elements can preferably be uniformly, in particular identically, configured. Simple geometric relationships for the design of the mobility and simple production can thus be achieved. Furthermore, the guide elements can be designed to be multi-part, in particular connected via an axial support structure, or in a single part as a coherent skeleton. A multi-part design can, for example, have the advantage of a variable overall length—at least during production. A single-part design can, for example, have the advantage of simple production and assembly.

However, the shape of the guide elements can also change, for example, along a longitudinal axis of the flexible section. This enables good adaptability to special forms of movement.

In addition, the guide elements can be supported against one another either inside or outside, in particular mediated by an axial support structure, as will be explained in more detail below.

The tip segment of the endoscope, which in particular can carry image capturing optics and/or illumination optics or other elements, can directly adjoin the flexible section distally. The distal end region can consequently comprise the flexible section and the tip segment.

Here, it is preferred for an investment composition that is used in order to form the flexible section (which will be described in more detail below) to extend into the tip segment. In this case, the investment composition contributes to forming the flexible section as well as the tip segment.

The flexible endoscope can also comprise numerous other components, such as a handle, an enveloping tube, a proximal stabilization tube, manipulators such as levers and/or (micro)motors (e.g. in robotics) in order to control the angling of the tip segment, as well as electrical, optical, or pneumatic connections or sluices for the taking of samples.

The skeleton itself can be designed in such a way that each of the guide elements guides the at least one tension cord. However, embodiments can also be provided in which only some of the guide elements guide a tension cord, while other guide elements guide a different tension cord.

The formation of a skeleton has the advantage, on the one hand, that a respective radial position and/or position of the at least one tension cord, i.e. in particular of a plurality of tension cords, can be precisely specified within the flexible section by means of the guide elements.

On the other hand, the skeleton gives the flexible section mechanical stability, but nevertheless enables a high degree of mobility, in particular the realization of small curvature radii during actuation. This is a great advantage especially when using a very soft investment composition, because the latter alone cannot provide sufficient mechanical stability.

A preferred direction of movement of the flexible section can also be defined by a corresponding configuration of the guide elements, because the guide elements can be designed to be more rigid in certain regions and more flexible in other regions, depending on the configuration. This makes the movement of the flexible endoscope more reproducible overall, in terms of precise controllability of the distal tip segment.

This results on the one hand in high reproducibility and good controllability of the movement of the tip segment as well as great mobility of the same when it is actuated via the at least one tension cord, i.e. rotated and/or angled, for example, in order to be able to visually inspect regions of hollow organs that are difficult to reach during a medical examination.

On the other hand, with the aid of the skeleton, it can be effectively avoided that, when the tip segment is actuated via tension cords, individual tension cords shear or tear out of the flexible section and then come into unintentional contact with tissue and injure the tissue, for example during a medical examination. Such a tear-out can occur without the use of a skeleton, for example, when the tension cords are only invested in a soft polymer material and are then subjected to strong tensile forces during the actuation. The skeleton thus enables a more reproducible and more precise transfer of forces with the aid of the tension cords onto the tip segment and/or onto the guide elements (as will be explained in more detail below).

In order to enable such a precise force transfer, respective tension guides in the guide elements can, in particular, be designed in such a way that they each define a radial position and/or an angular position of the at least one tension cord in relation to a neutral fiber of the flexible section. A neutral fiber can be understood here, in particular, as a longitudinal layer within the flexible section, the length of which does not change when the flexible section is twisted or bent. In the case of a symmetrical configuration of the flexible section in the form of a cylinder, for example, the neutral fiber lies directly in the center of the cylinder and coincides with the longitudinal axis of the cylinder.

The tension cords can preferably run parallel to one another in the direction of a longitudinal axis of the flexible section when the flexible section is aligned in a resting position in which the tip segment lies opposite a proximal abutment, which in turn adjoins the flexible section proximally. With the aid of the tension guides of the guide elements, however, more complex profiles of the tension cords can also be achieved in this position, for example obliquely angled or (at least slightly) spiral profiles.

For good controllability of the endoscope, it is generally preferable for each of the guide elements to have a plurality of tension guides, because a respective guide element can, in particular, define a relative position between different tension cords which run through the flexible section.

In order to control the tip segment, the at least one tension cord can be connected to the tip segment directly or indirectly, i.e. in particular in a force-fit and/or materially cohesive manner. The tip segment can thus serve as a distal counter bearing for the at least one tension cord.

According to preferred embodiments, the flexible endoscope comprises at least two tension cords, which are guided by the guide elements and by means of which the distal tip segment can be angled or aligned in different spatial directions. However, configurations with four tension cords can also be realized, for example.

By means of the at least one tension cord or the at least two, preferably three tension cords, the tip segment can be controlled by bending the flexible section, that is to say in particular it can be angled or aligned in different spatial directions.

In order to form the skeleton, in particular as an endoskeleton, the guide elements can preferably be lined up along the neutral fiber, preferably at regular intervals.

The skeleton of the flexible section can basically be designed as an internal skeleton (endoskeleton) or an external skeleton (exoskeleton).

If the skeleton is designed as an exoskeleton, the guide elements can form an outer shell of the flexible section and can, in particular, be designed to overlap and/or slide against one another, for example in the form of overlapping annular sleeves. In such a configuration, the aforementioned tension guides can be designed in order to guide the tension cords on respective inner surfaces of the guide elements.

However, a design as an endoskeleton is preferred, as this design enables smaller curvature radii, as will be explained in more detail below.

In both cases, in particular when the skeleton is designed as an endoskeleton, an axial support structure can be provided. The axial support structure can namely be used for the axial fixing of the guide elements along a longitudinal axis of the flexible section/along the aforementioned neutral fiber.

Here, the axial support structure can remain in the endoscope as part of the latter (for example, when the axial support structure is designed as a support tube with a working volume). In other configurations, however, the axial support structure can be present merely temporarily for the production process ("volatile form"). Furthermore, the axial support structure can also be formed by a plurality of structures.

In addition to the fixing of the guide elements, the use of an axial support structure may also be necessary for uniform and homogeneous movement of the distal tip segment. Furthermore, an axial support structure can prevent the flexible section from being compressed when the tension cords are pulled.

For this purpose, axial fixings can, in particular, be formed between the axial support structure and the guide elements. These fixings can be designed, for example, in the form of depressions or bulges and/or with the aid of snap-in structures that enable the guide elements to snap onto the axial support structure. Similar to vertebrates, an endoskeleton can thus be built up, in which the guide elements are lined up along the axial support structure, preferably at regular intervals, with the aid of the axial fixings.

The axial support structure can advantageously be designed as a support tube with an internal working volume. Such a configuration is suitable for endoscopes with which pieces of tissue are to be removed from an interior space through the working volume. In applications in which such removals are not necessary, the axial support structure can be designed, for example, as a flexible core.

The axial support structure can provide cross-connections between the guide elements. These cross-connections can be used in particular for stabilization, during the insertion of the skeleton into an investment mold, and before the skeleton is invested in an investment composition such as silicone. The cross-connections/the axial support structure can also ensure a preferred direction, which results in a defined and uniform movement of the flexible section when the tip segment is actuated via the tension cords.

The working volume of the support tube can be designed as a working channel, in particular. For this purpose, the working volume can flow into a distal outlet of the distal tip segment, preferably designed as a continuous channel. In such a case, the distal exit can be at least partially formed by the investment composition. Thus, an entire working channel of the endoscope can be formed by the working channel that is formed in the flexible region and the distal exit of the distal tip segment. The distal exit can be obtained, for example, by investment of a mandrel into the investment composition during the investment process, which is subsequently removed. In this case, the mandrel defines an internal volume of the distal exit. The working channel of the endoscope can be set up, for example, as a suction channel and/or as a flushing channel for flushing with flushing liquid and/or as an instrument channel for inserting instruments into cavities that are examined with the endoscope.

The axial support structure, which, in a scenario that is particularly good for movement, lies in the neutral fiber, can also comprise electrical voltage supply lines and/or data lines. Alternatively, the axial support structure can also be in the form of a tube and thus also serve for the transport of liquid or gas.

The aforementioned electrical connection lines can, for example, serve to supply an image sensor and/or a light source and/or be set up for bidirectional data transport.

An extremely preferable variant that significantly improves the stability of the flexible section provides for the skeleton to be (at least partially) invested into an investment composition that also forms the flexible section. The investment composition preferably consists of an initially liquid elastomer that is cured by the necessary cross-linking processes. Silicones, for example, which also meet typical requirements for biocompatibility, are suitable for this purpose.

It is particularly preferable for the investment composition to penetrate into the distal tip segment and to contribute to forming the distal tip segment. This has the advantage that the investment composition and thus the flexible section can be securely anchored to the tip segment, because, after the investment composition has cured, these tensile and compressive forces can be transferred from the flexible section to the tip segment.

In addition, the investment composition can assume additional functions in the tip segment. For example, the investment composition can be used in order to invest sensitive electronic components, such as image sensors, other sensors, or light sources, in the tip segment and/or to dissipate heat loss from these components, and/or the investment composition can act as an optical element there, for example in order to enable a diffuse illumination by means of a commercially available LED. Here, the investment of the components can be understood, in particular, to mean that these components are fixed, in particular in a preferred position and/or orientation, within the distal tip segment by means of the investment composition. Proceeding from this concept, optical fibers can also be invested in the investment composition instead of light sources such as LEDs. These optical fibers guide the light from a light source (or from an external light source) arranged in the proximal endoscope region (for example, in a handle) to the distal end of the endoscope.

In such configurations, for a high mechanical stability of the flexible region, it is preferable when the investment composition fills the interstices between the guide elements, because, in this case, the investment composition can support the guide elements against one another and thus, in particular, transfer actuation forces from guide element to guide element. The mutual supporting of the guide elements also prevents the flexible section from being compressed during the actuation of the tension cords.

A coherent endoskeleton can preferably be produced by injection molding or by additive production processes. It is particularly advantageous when an investment composition located between the guide elements, similar to intervertebral discs of a spinal column, has a lower hardness and higher elasticity than the skeleton.

Here, the guide elements can be supported against one another internally and/or externally, in particular by means of the investment composition. In particular, the investment composition can thus fill interstices between the guide elements in order to enable a transfer of forces from one guide element to a respectively adjacent guide element.

The investment composition can preferably be formed from a flexible material, in particular an elastomer material such as silicone. Thus, in particular, an endoskeleton consisting of a large number of guide elements can be invested into a flexible material in order to form the flexible section.

The investment composition, which is preferably formed by an elastically deformable material, can thus be formed with the aid of an investment process. In particular, the investment composition can thus be a casting material, in particular an injection molding material, and/or be formed by means of a casting process, in particular by means of an injection molding process. Vacuum casting processes can also be used for this purpose. The investment composition can thus be cast or poured into interstices of the skeleton, in particular injection molded or vacuum molded and/or through the use of two components.

For high mobility of the distal end region of the endoscope, it is particularly advantageous when the investment composition has a lower, preferably more than ten times lower, hardness than the material from which the skeleton is constructed. The investment composition can then take on a function similar to the intervertebral discs in a spine.

Another embodiment provides that the investment composition is designed as a two-component investment composition, preferably by means of a two-component injection molding. This makes it possible to achieve high mobility of the flexible section with simultaneously good mechanical stability. For this purpose, the axial support structure can preferably be formed with the aid of a first component of the two-component investment composition. This component can be more rigid than a second component of the two-component investment composition. The softer second component can form the outer regions of the flexible section.

According to further configurations, the guide elements can each be designed in a disc-shaped and/or rigid manner (compared to the investment composition).

The guide elements can be spaced apart from one another, preferably at regular intervals. In this case, the investment composition can transfer tensile and/or thrusting forces between adjacent guide elements.

In the case of a configuration as an endoskeleton, it is further advantageous for good guidance of the tension cords when the guide elements are aligned transversely to a running direction of the at least one tension cord, that is to say in particular transversely to a longitudinal axis of the endoscope. It is also understood that the guide elements are preferably arranged within the flexible section.

For a high stability of the skeleton, it is also advantageous when directly adjacent guide elements are, in each case, at most as far apart from one another as their respective diameter.

The guide elements, or their tension guides, can preferably be designed in such a way that they each support forces applied radially inwards and/or radially outwards from the at least one tension cord, i.e. in particular from a plurality of tension cords. This is especially true when the tension cord is completely inserted into a corresponding tension guide of the respective guide element. This can prevent the at least one tension cord from cutting into the aforementioned investment composition or into the tissue adjoining the flexible section when the tip segment is actuated, because the tension cord is held by the skeleton in the relative position that is desired for the actuation.

According to a preferred embodiment, the guide elements can be designed in such a way that they do not support the respective tension cord at least at a respective insertion point. Such a configuration can enable the tension cords to be inserted laterally into the guide elements of the already assembled skeleton, which results in a simplified assembly of the endoscope.

A specific embodiment proposes that the guide elements each form passages for the tension cords in order to guide them. It is then similarly preferable for a simplified assembly when the tension cords can be inserted into the passages from the outside transversely to their respective running direction.

In further configurations, the passages can be designed in such a way that the tension cords, in particular end heads attached to their ends for fixing in the tip segment or in a proximal counter bearing, can be inserted into the passages along their running direction.

In both of these cases, it is particularly preferred for the passages to each have support surfaces arranged radially on the outside in order to support forces that are applied radially outwards from the tension cords.

For a simple assembly of the endoscope, it can therefore be provided that the at least one tension cord, in particular the aforementioned plurality of tension cords, can be inserted transversely to a longitudinal axis of the endoscope in tension guides, in particular the aforementioned passages, of the guide elements.

In this case, the guide elements on the tension guides/passages can each form a holding device in order to prevent the respective tension cord from escaping from the tension guide. Such a holding device can preferably be formed by means of a clamping or crimping mechanism. Alternatively or additionally, the guide elements can also be elastically or plastically deformable in order to form the holding device in the region of the tension guides.

In order to reduce friction losses between the at least one tension cord and the investment composition, in particular the aforementioned flexible material, when controlling the tip segment, the at least one tension cord, i.e. in particular the aforementioned tension cords of the endoscope, can each comprise sections between the guide elements that are not covered by the investment composition. In other words, with this special guiding of the tension cords, a respective section of a tension cord can run outside of the investment composition in some regions. Such a guiding of the tension cords is also advantageous in order to enable very small bending radii in the region of the flexible section, because, in previous approaches, the unavoidable displacement of flexible material of the flexible section has always limited the curvature of the same. By creating free spaces, which can be designed in particular as lateral, preferably circumferential, indentations in the investment composition, greater freedom of movement can be created for the flexible section. Such an endoscope can thus penetrate into regions of bodily cavities that are very difficult to access (for example, paranasal sinuses, etc.), which decisively improves the application possibilities of the endoscope.

A particularly favorable ratio between sufficiently high mechanical stability and high freedom of movement of the flexible section results when an aspect ratio, as a ratio of a distance between the guide elements to a radial height of an exposed region, does not exceed a value of 2:1.

In order to increase the mobility of the flexible section, a preferred embodiment proposes that the flexible section comprise a plurality of at least partially circumferential indentations. These indentations can preferably be formed in the investment composition and can also be covered by an enveloping tube.

In particular, the indentations can be configured by casting of the investment composition, that is to say, in particular by injection molding or vacuum casting and/or through the use of two components.

Furthermore, it is of great advantage for high mobility of the flexible section in different spatial directions when the indentations follow circular paths, partial circular paths, or helical lines (or parts thereof). The advantage of such a configuration is that very small curvature radii can be realized in the region of the flexible section.

The aforementioned indentations, which can be embodied as constrictions, in particular, can furthermore preferably be aligned at right angles to a respective angulation plane of the endoscope in which the flexible section can be angulated. Furthermore, the indentations/constrictions can also be arranged alternately offset from one another. This is particularly advantageous when using four tension cords in order to ensure high flexibility of the flexible section.

As mentioned above, it is advantageous for a simple production when the investment composition is designed as a casting compound or as an injection molding compound in the injection molding process or is introduced by means of vacuum casting, because, in such methods, the guide elements can be particularly easily encased, at least partially, by the investment. It is particularly advantageous when the investment composition forms a continuous connection over the entire flexible section, because it can be introduced in a single production step.

It has also already been mentioned that the investment composition can consist of a plurality of material components, in particular a plurality of material layers. These components or layers can be formed, for example, by multi-component injection molding or multi-component molding. This opens up further design options in order to optimize the mechanical properties of the flexible section, depending on the application and control design. For example, it is thus possible to pair different material properties, for example different hardnesses or transparency/non-transparency, in the flexible region.

In order to achieve good controllability of the flexible endoscope, it can be provided that at least two, preferably at least four, tension cords are formed. In particular, each of the guide elements can guide at least one of the at least two tension cords, preferably at least two of the at least four tension cords. Furthermore, the tension cords can each be connected to a distal counter bearing in the distal tip segment of the endoscope in a tension-resistant manner. This counter bearing can be formed, for example, by a carrier body in the distal tip segment.

Alternatively or additionally, the tension cords can also be connected to individual guide elements. This enables further complex forms of actuation.

Thus, at least two tension cords can preferably be provided, which can in particular be designed as cables, by means of which the flexible section can be aligned in different spatial directions, in particular so that different spatial directions can be observed with image capturing optics arranged in the tip segment.

In general, for a particularly simple handling/control of the flexible endoscope, it is preferable to use an even number of tension cords. According to a preferred embodiment, the endoscope has at least four tension cords for angulating the flexible section. In this case, it is advantageous when each of the guide elements guides at least three of the at least four tension cords.

The guide elements can be produced in a particularly cost-effective manner together in a batch process. Depending on the design, the guide elements can also be produced individually as single parts.

A batch processing of the guide elements can include, for example, the processing of an intermediate product from which the individual guide elements are obtained through separation. For example, the guide elements can be obtained from an intermediate product in the form of a cylindrical body through separation into wafers, for example by sawing/eroding. The contour of the intermediate product can have been defined beforehand, for example by means of processes such as water jet cutting/laser cutting/plasma cutting/punching/sawing/etching/eroding in the cord.

On the other hand, processes such as water jet cutting/laser cutting/plasma cutting/punching/sawing/injection molding or hot stamping, to name just a few, are suitable for the production of single parts of the guide elements.

In order to solve the aforementioned problem, the features of the independent method claim are additionally provided according to the invention. In particular, in order to solve the problem in a method of the type described above, it is proposed according to the invention that a plurality of preferably rigid and/or disc-shaped guide elements for guiding at least one tension cord of the endoscope to a skeleton are lined up even before the skeleton is (at least partially) invested into an investment composition. In this case, the investment can in particular take place in that the investment composition is casted, preferably injection molded, into the skeleton.

The advantage of this method is that a highly complex structure of the flexible section can be produced in a particularly simple and cost-effective manner, wherein the aforementioned structure enables the endoscope to be controlled with high precision.

The method can be even further improved when the guide elements are aligned and held in position during investment in the investment composition by an investment mold that is used for this purpose, because the desired mechanical function of the skeleton can thus be ensured. Such an investment mold can also be a so-called sacrificial structure. Such a volatile sacrificial structure, which can be made of wax, for example, is only used once for the assembly and investment process and is subsequently removed (e.g. by melting).

Furthermore, for the simplest possible and thus most inexpensive assembly, it is advantageous when the aforementioned at least one tension cord, i.e. in particular a plurality of tension cords of the endoscope, is invested in a (respective) inserted position of the investment composition.

For this purpose, two basic approaches can be pursued, which can also be combined with one another:

On the one hand—even before the skeleton is invested into the investment composition—the at least one tension cord can be introduced into tension guides of the guide elements along a longitudinal axis of the endoscope.

It is preferred, however, when—even before the skeleton is invested into the investment composition—the at least one tension cord is inserted laterally in tension guides of the guide elements transversely to a longitudinal axis of the endoscope. For this purpose, the tension guides must naturally be designed in such a way that a lateral insertion is possible transversely to an extension direction of the respective tension cord. In this case, it is preferable for the tension cords to then be held in position in the tension guides by means of holding devices, which are formed on the guide elements and which have already been described in detail.

In order to assemble the skeleton before investment, it is helpful for simple assembly when the guide elements are lined up to form the skeleton by threading of the guide elements onto the tension cords of the endoscope and/or onto an axial support structure, as already described above.

According to a preferred variant of this method, the guide elements and/or a distal tip segment of the endoscope are designed in such a way that all components that run through the flexible section of the endoscope and are at least partially invested by the investment composition—such as light guides, electrical connection lines, or the tension cords—can be inserted laterally from the outside into the guide elements and optionally the tip segment. The advantage of this variant is that it is not necessary to thread the guide elements onto these components. This variant is particularly useful when the number of the aforementioned components is large.

According to a further preferred variant, an investment or casting mold that is used for investing of the skeleton comprises recesses for receiving at least partial regions of the at least one tension cord. As a result, it can thus be achieved that, after the flexible section has been formed by investment of the skeleton and the tension cords into the investment composition, at least these partial regions of the at least one tension cord are not covered by the investment. As a result—as already explained in detail above—the mobility of the flexible section can be improved.

The invention will now be described in more detail on the basis of exemplary embodiments, but is not limited to these exemplary embodiments. Further developments of the invention result from the combination of the features of individual or multiple claims with one another and/or with individual or multiple features of the exemplary embodiments.

BRIEF DESCRIPTION OF THE DRAWINGS

The following are shown.

DETAILED DESCRIPTION

Figure 1:
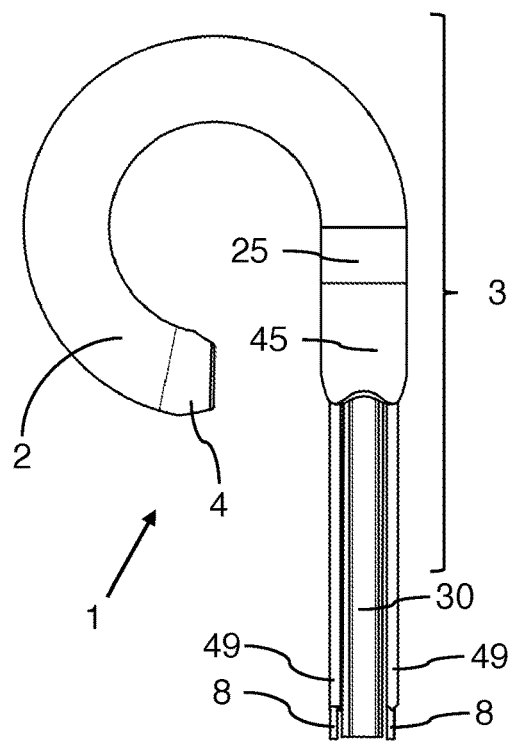
FIG. 1 a plan view from above of an endoscope tip of a flexible endoscope according to the invention,
FIG. 2 a further view of the endoscope from FIG. 1,
FIG. 3 a further view of the endoscope from FIG. 1,
FIG. 4 a further view of the endoscope from FIG. 1,
FIG. 5 a further view of the endoscope from FIG. 1,
FIG. 6 a further view of the endoscope from FIG. 1,
FIG. 7 a further view of the endoscope from FIG. 1 with a fully stretched flexible section and a detailed view of the distal tip segment of the endoscope,
FIG. 8 a further view of the endoscope from FIG. 7,
FIG. 9 a further view of the endoscope from FIG. 7, with a enveloping tube removed so that the view of the skeleton below is clear,
FIG. 10a side view of the endoscope from FIG. 7,
FIG. 11 a further side view of the endoscope from FIG. 7,
FIG. 12 to FIG. 17 various possible configurations of the tip segment of the endoscope,
FIG. 18 a partial longitudinal section through the endoscope according to FIG. 1,
FIG. 19 a detailed view B of the longitudinal section from FIG. 18,
FIG. 20 a single guide element of the skeleton of the endoscope from FIG. 18,
FIG. 21 another view of the endoscope from FIG. 18, this time only with the enveloping tube removed, so that the view of the investment composition underneath, which partially envelops the skeleton, is clear,
FIG. 22 a detailed view of the view according to FIG. 21, viewed from above, FIG. 23 the endoscope from FIG. 21 in the same view but with an angled flexible section, FIG. 24 a further endoscope according to the invention in a partial longitudinal sectional view, FIG. 25a detail A of the view from FIG. 24, FIG. 26 a further detailed view of the endoscope from FIG. 24, FIG. 27 a single guide element of the skeleton of the endoscope from FIGS. 24 and 26, which is designed in such a way that tension cords can be inserted laterally from above into tension guides of the guide element, FIG. 28 a further endoscope according to the invention in a partial longitudinal sectional view, FIG. 29a detail A of the view from FIG. 28, FIG. 30 a further detailed view of the endoscope from FIG. 28, FIG. 31 a single guide element of the skeleton of the endoscope from FIGS. 28 and 30, which is designed in such a way that tension cords can be introduced into tension guides of the guide element along a longitudinal axis of the endoscope, FIG. 32 to FIG. 40 various designs of guide elements, wherein various types of holding devices for the tension cords are shown, FIG. 41 a longitudinal section through the flexible section of an endoscope according to the invention and its anchoring in a proximal counter bearing, FIG. 42 another possible manner of anchoring a flexible section of an endoscope according to the invention in a proximal counter bearing, FIG. 43 another possible manner of anchoring a flexible section of an endoscope according to the invention in a proximal counter bearing, FIG. 44 a skeleton of an endoscope according to the invention with two tension cords, designed for a 2-fold angulation, before investment in an investment composition, FIG. 45 a detailed view of the skeleton from FIG. 44, FIG. 46 a skeleton of an endoscope according to the invention with four tension cords, designed for 4-fold angulation, before investment in an investment composition, FIG. 47a detailed view of the skeleton from FIG. 46, FIG. 48 a skeleton of an endoscope according to the invention with a number of more than four tension cords, designed for multiple angulation, before investment in an investment composition, FIG. 49 a detailed view of the skeleton from FIG. 48, FIG. 50 an illustration of possible angulations of the endoscope from FIG. 46, FIG. 51a further illustration of possible angulations of the endoscope from FIG. 46, FIG. 52 an example of an exoskeleton according to the invention for an endoscope according to the invention, FIG. 53a view from above of the exoskeleton of FIG. 52, FIG. 54 an example of an endoskeleton according to the invention for an endoscope according to the invention, wherein the skeleton has an axial support structure, FIG. 55 a view from above of the endoskeleton of FIG. 54, FIG. 56 a further example of a skeleton of an endoscope according to the invention, FIG. 57a detailed view of the skeleton from FIG. 56, FIG. 58 a longitudinal sectional view of the skeleton from FIG. 56, FIG. 59a detailed view of the longitudinal section from FIG. 58 showing the axial fixing of the guide elements on the axial support structure.
Figure 2:
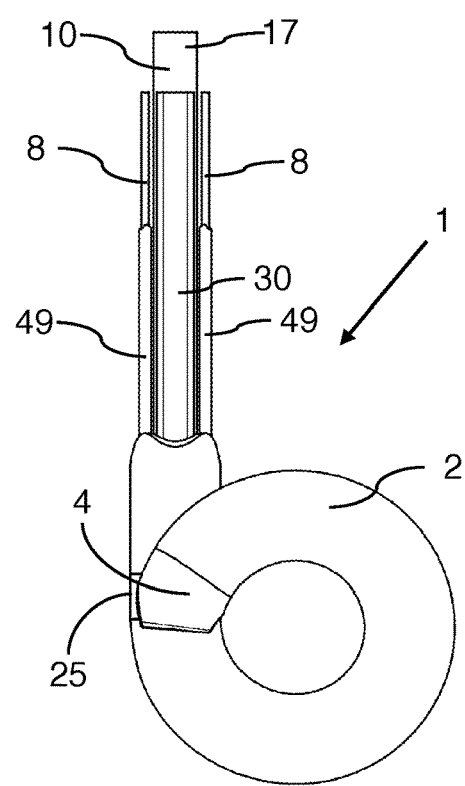
Figure 3:
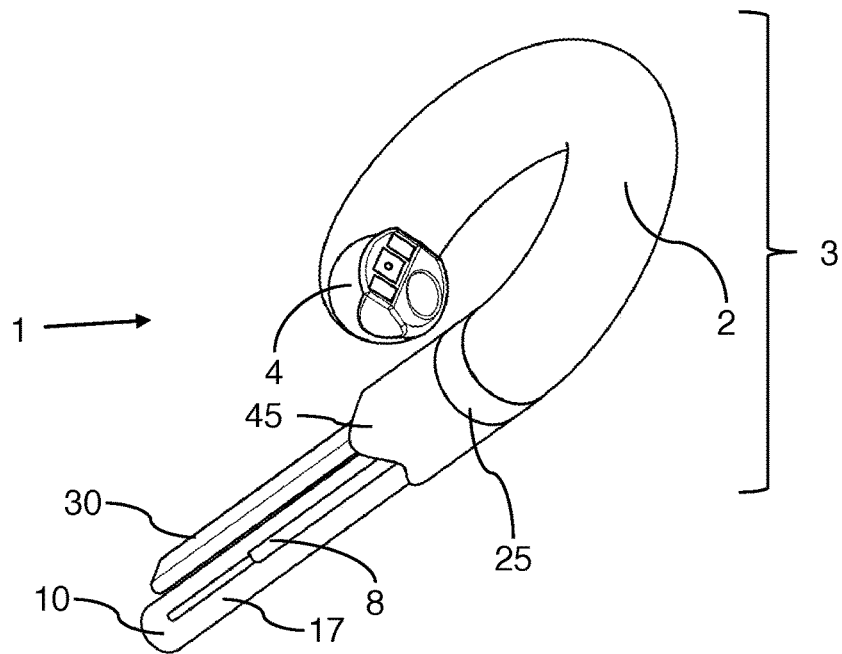
Figure 4:
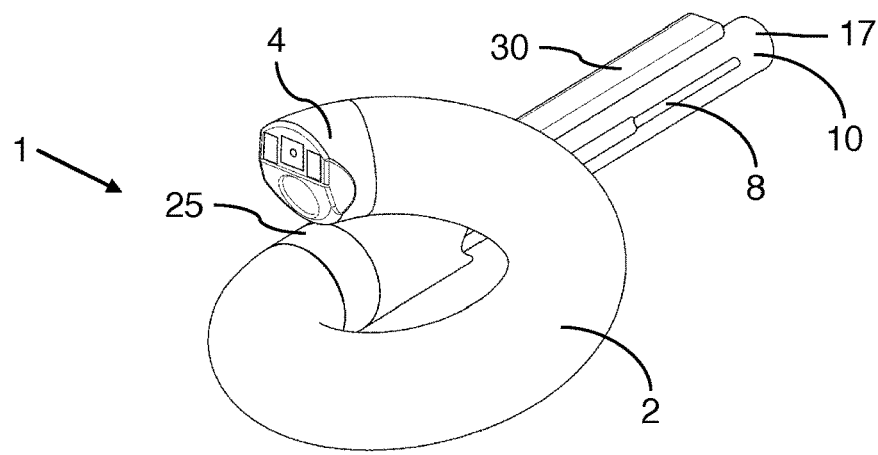
Figure 5:
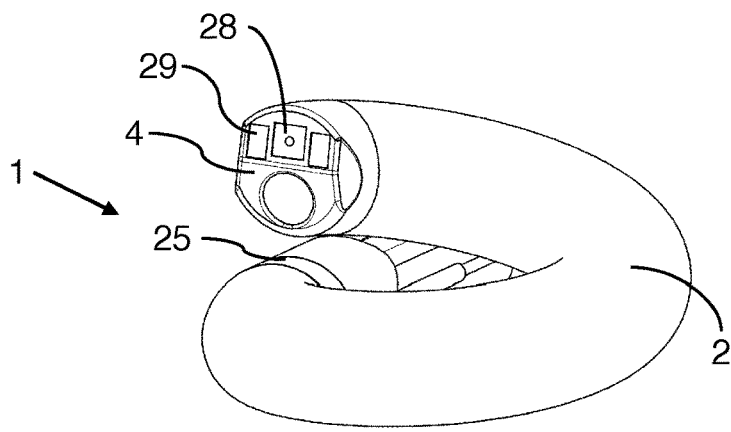
Figure 6:
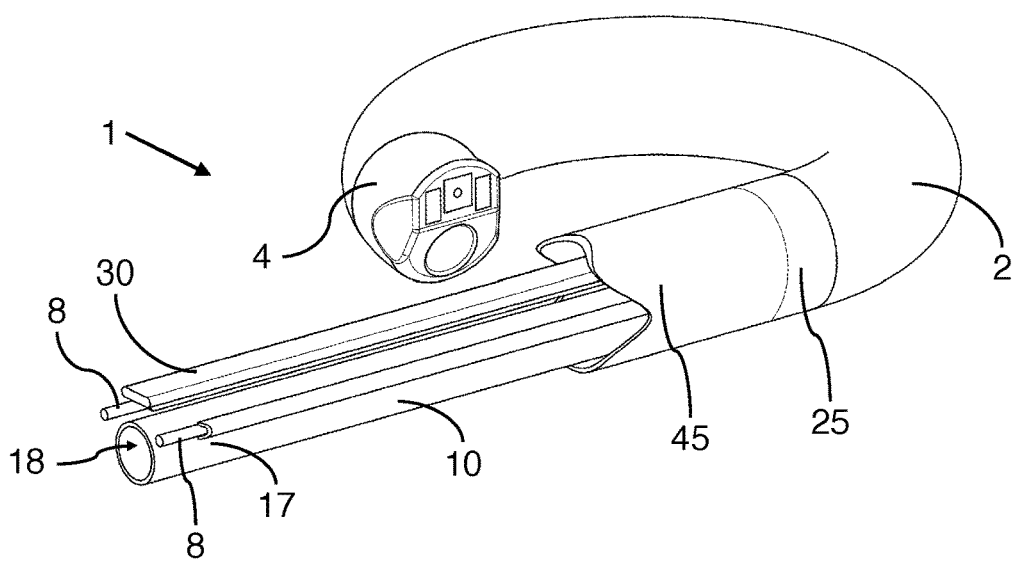
Figure 7:
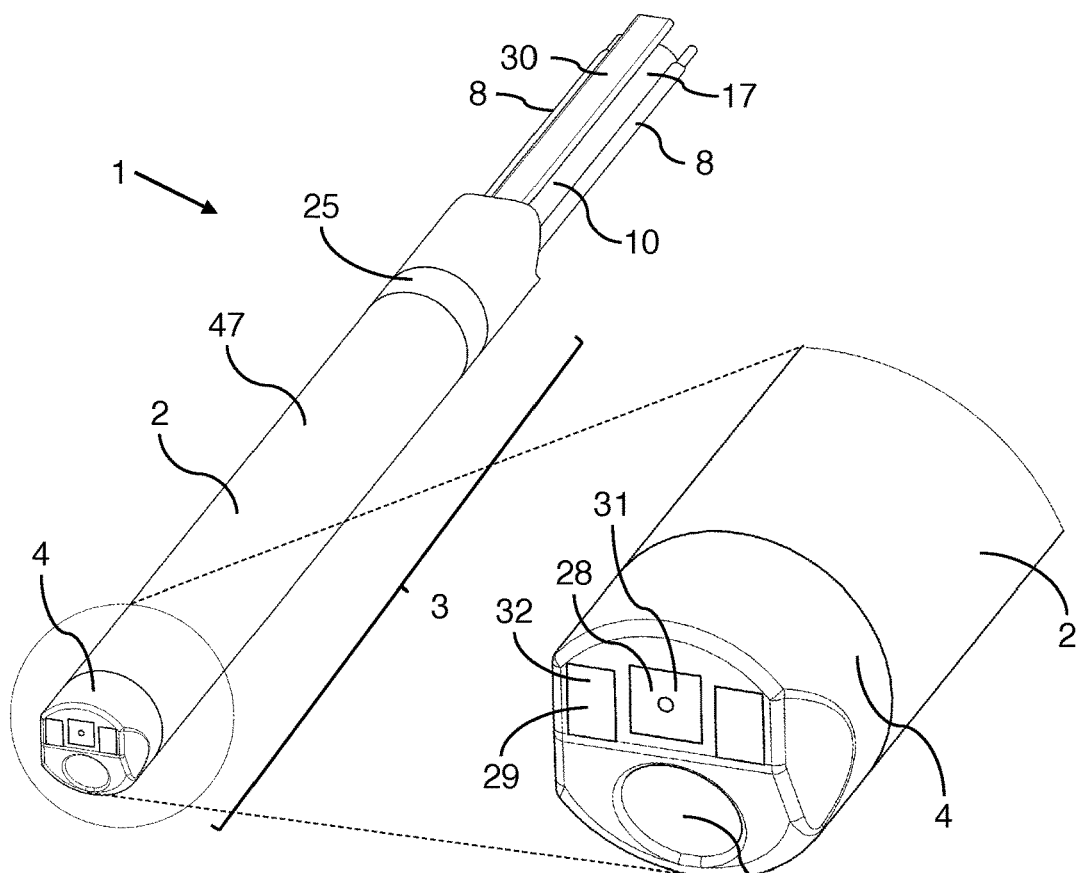
Figure 8:
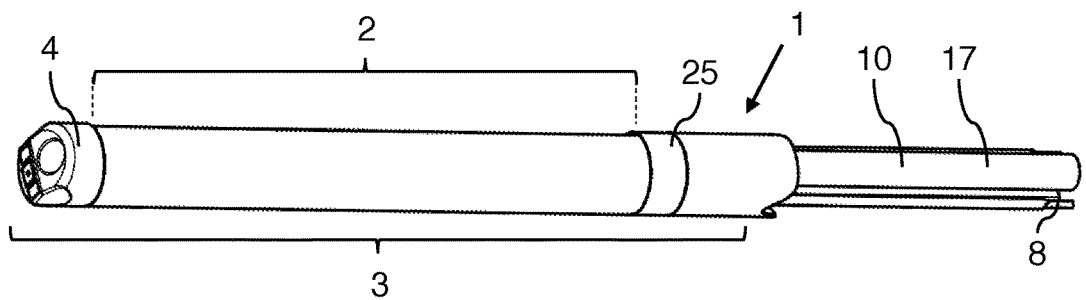
Figure 9:
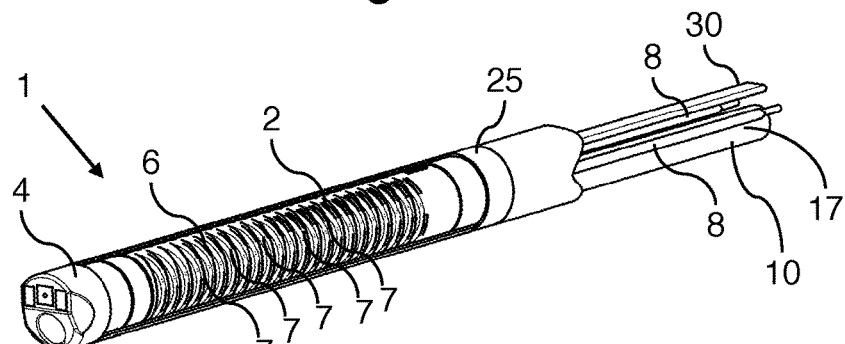

In the following description of various preferred embodiments of the invention, elements with corresponding functions are given the same reference numbers, even if they have a different design or shape. The figures are therefore initially described together, and the differences between the exemplary embodiments are discussed below. The explanations then apply accordingly.

The figures each show the endoscope tip, that is to say a distal end region 3 of a flexible endoscope 1 or parts thereof. The various endoscopes 1 shown are designed to be inserted into the human body or into another cavity (for non-medical applications).

For this purpose, the endoscopes have a flexible section 2, which is arranged in a distal end region 3 of the endoscope 1.

A distal tip segment 4 adjoins the flexible section 2.

The tip segment 4 can be controlled in a manner known per se by means of at least one tension cord 8.

In the embodiments according to the invention, the flexible section 2 has a skeleton 6, which has a large number of guide elements 7. These guide elements 7 guide the tension cords 8 in such a way that their position is fixed transversely to the longitudinal direction of the endoscope 1, that is to say radially, and in the circumferential direction.

For this purpose, the respective tension guides 9 of the guide elements 7 each define a radial position 11 and/or an angular position 12 of the at least one tension cord 8.

Here, the radial position 11 and/or the angular position 12 can be defined in relation to a neutral fiber 13 of the flexible section 2.

The guide elements 7 are lined up, preferably at regular intervals, along the neutral fiber 13, which can define a longitudinal direction of the endoscope 1. However, the distances can also be of different sizes, depending on the configuration.

For simple production, it is preferable for the guide elements 7, as illustrated in the figures, to be designed in order to be identical to one another. However, particularly in the case of endoscopes that allow multiple angulations, it can be useful to assemble guide elements 7 that are not identical, that is, differently configured, in order to form a skeleton 6.

Figure 18:
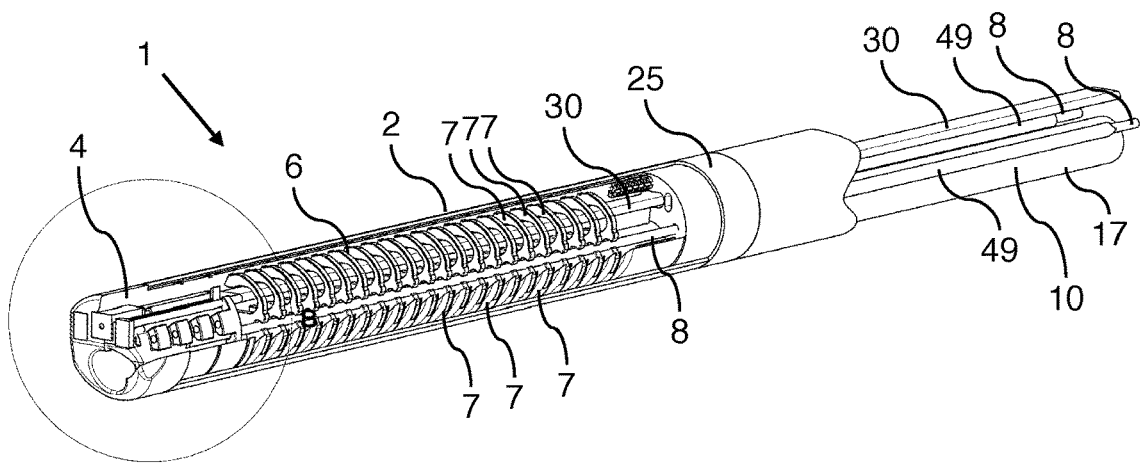
Figure 54:
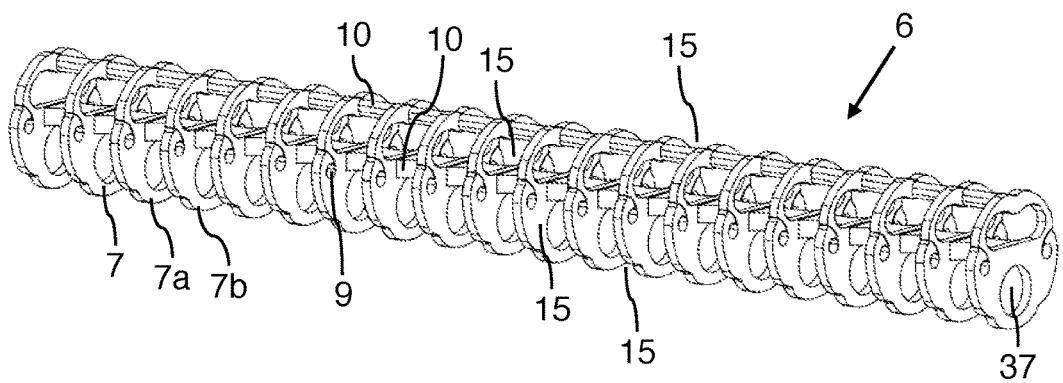
Figure 55:
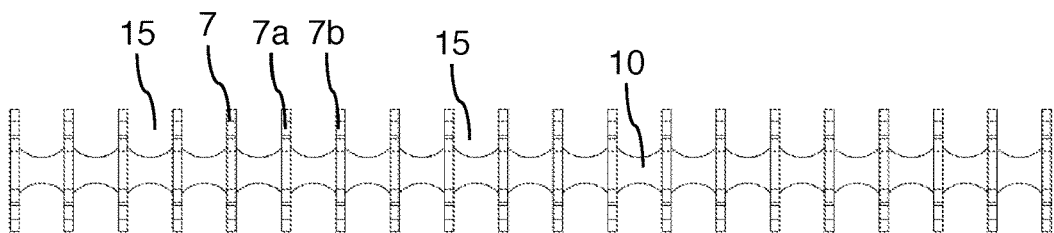
Figure 56:
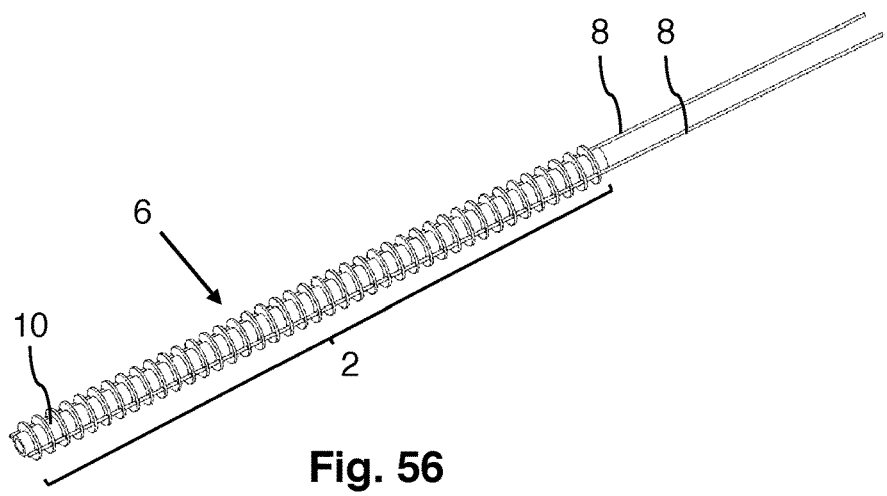
Figure 57:
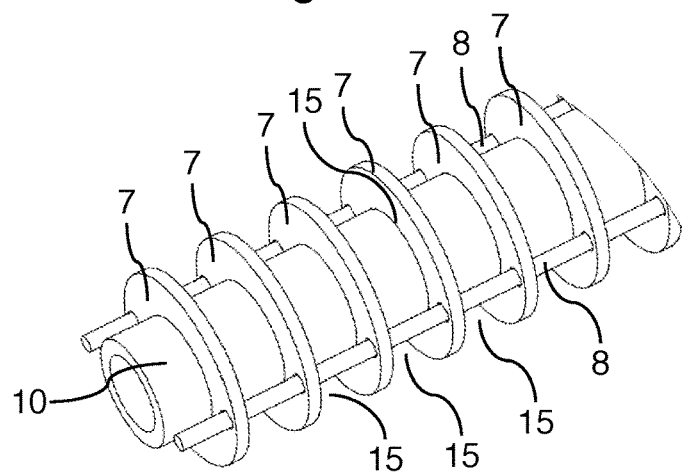
Figure 58:
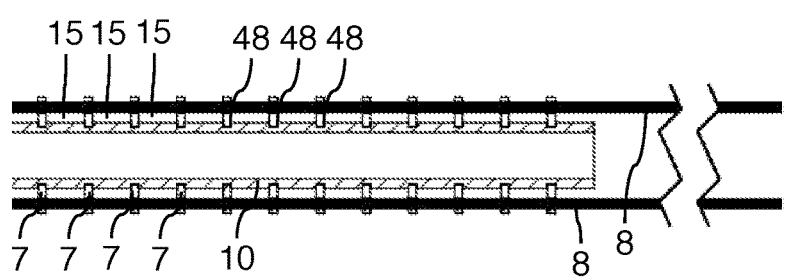
Figure 59:
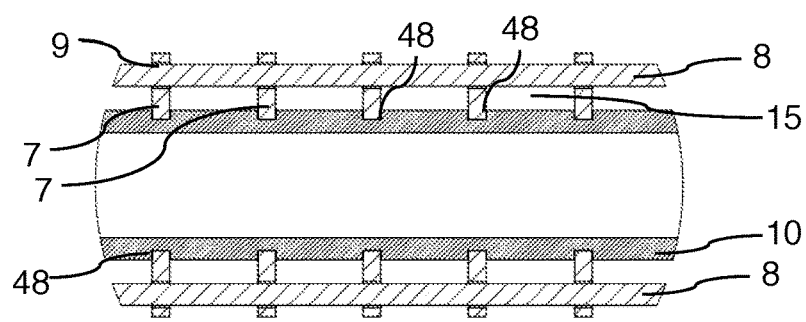

The skeleton 6 (e.g. in FIG. 18) is designed as an endoskeleton (i.e. it is not part of an outer shell) and has an axial support structure 10, which is used in order to axially fix the guide elements 7 along a longitudinal axis 16 of the flexible section 2. However, as shown by FIG. 54, the axial support structure also can be formed by a plurality of structures.

The axial support structure 10 has (at least) one support tube 17 with (at least one) internal working volume 18 or (at least one) working channel 35 and forms a flexible core, which—without a working volume—can be designed free of cavities. The working channel 35 can form a receptacle 37 for instruments.

FIG. 17 shows a variant with an additional flushing and/or instrument channel 36. The latter can also be integrated into the working channel 35.

The skeleton 6 is invested into an investment composition 14. This investment compound 14 also forms the flexible section 2 and defines its mobility or flexibility.

As used herein, the terms "invest," "investing," and "invested," refer to embedding, molding, or otherwise surrounding/containing a component or structure within a material, such as, for example, a component of a flexible endoscope within another component or structure of the endoscope.

The term "investment composition" as used herein refers to a soft, flexible material into which other components or structures may be invested, e.g., molded, embedded or otherwise surrounded by/contained within the material. The investment composition may be a polymer such as silicone, into which, for example, a skeleton 6 of an embodiment, may be molded/embedded, either by injection molding, by a casting process, or by other techniques, such as, for example, processes where the investment composition is initially a liquid and then is solidified into a mass, via UV curing, a curing agent, and the like. As described in greater detail herein, the investment composition may be a single material such as a temperature-curing, one-component silicone, or a multiple component composition such as a two-component epoxy or silicone.

In this case, the investment composition 14 fills the interstices 15 between the guide elements 7 at least partially or even completely. The guide elements 7 are thus supported against one another.

The investment composition 14 is vacuum-cast (that is, cast using a negative pressure) or cast in some other way in the interstices of the skeleton 6.

The axial support structure 10 can also be cast, for example with the aid of a first component of a two-component investment composition. This first component can preferably (in the hardened state) be more rigid than a second component of the two-component investment composition. The latter can then form the investment composition 14 described above. As a result, sufficient mechanical stability is achieved by the first component, with simultaneous high flexibility due to the softer second component.

It can be seen from the figures that the guide elements 7 are each designed in the form of discs. The guide elements 7 are designed to be rigid and can stably absorb lateral forces that act on the tension cords 8 when subjected to tension stress.

Figure 19:
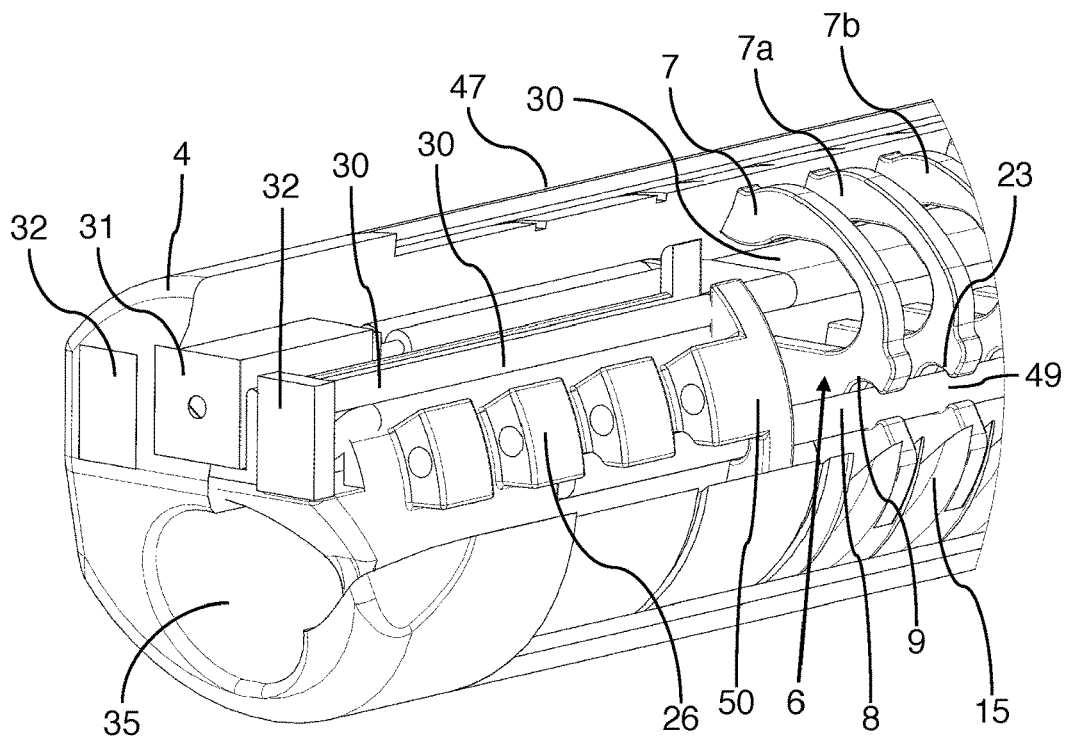
Figure 20:
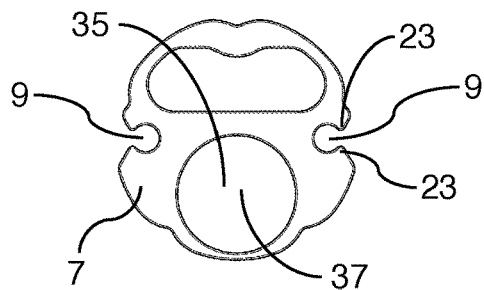

As can be seen for example in FIG. 19 or FIG. 54, it is advantageous for a high mechanical stability of the skeleton 6 when guide elements 7a, 7b, which are directly adjacent to one another, are at most as far apart from one another as their respective diameter.

For this purpose, the guide elements 7 lie transversely to a running direction 19 of the at least one tension cord 8, so that the respective tension cord 8 runs transversely through the guide element 7.

The guide elements 7 are thus aligned with a longitudinal axis 16 of the endoscope 1.

It can also be seen from the figures that the guide elements 7 are arranged within the flexible section 2 in order to stabilize it. Here, a distance between directly adjacent guide elements 7a, 7b is less than their respective diameter.

The flexible section 2 is controlled in a manner known per se by tensile and/or compressive stress on the tension cords 8. For this purpose, due to the current shape of the flexible section 2, each tension cord 8 develops lateral forces which can be directed radially inwards or outwards.

The guide elements 7 thus each support forces applied radially inwards and/or radially outwards from the tension cords 8 and thus prevent the tension cords 8 from cutting into the investment composition 14 when the tip segment 4 is actuated.

Here, the guide elements 7 do not support the respective tension cord 8 at least at a respective insertion point 20.

Furthermore, the guide elements 7 each form passages 21 for the tension cords 8. The tension cords 8 can thus be introduced from the outside transversely to their respective running direction 19. A threading is therefore not necessary.

In order to absorb the radial forces mentioned, the passages 21 each have support surfaces 22 arranged radially on the outside.

It can be seen that the guide elements 7 are shaped in such a way that the tension cords 8 can each be inserted or hooked into tension guides 9 of the guide elements 7 transversely to a longitudinal axis 16 of the endoscope 1.

For this purpose, a holding device 23 is formed on each of the tension guides 9 in order to prevent the tension cord 8 from escaping from the tension guide 9.

The securing device 23 has a clamping or crimping mechanism (crimping 27), wherein the guide elements 7 are elastically or plastically deformable in the region of the tension guides 9 in order to form the holding device 23.

Between the guide elements 7, there are sections 24 which are not covered by the investment composition 14 (cf. FIGS. 21-23 and 41-43). This reduces friction losses between the at least one tension cord 8 and the investment composition 14 when the tip segment 4 is controlled. The exposed sections 24 thus serve to keep the control forces for the angulation of the tip segment as low as possible and thus enable a particularly smooth angulation.

Figure 21:
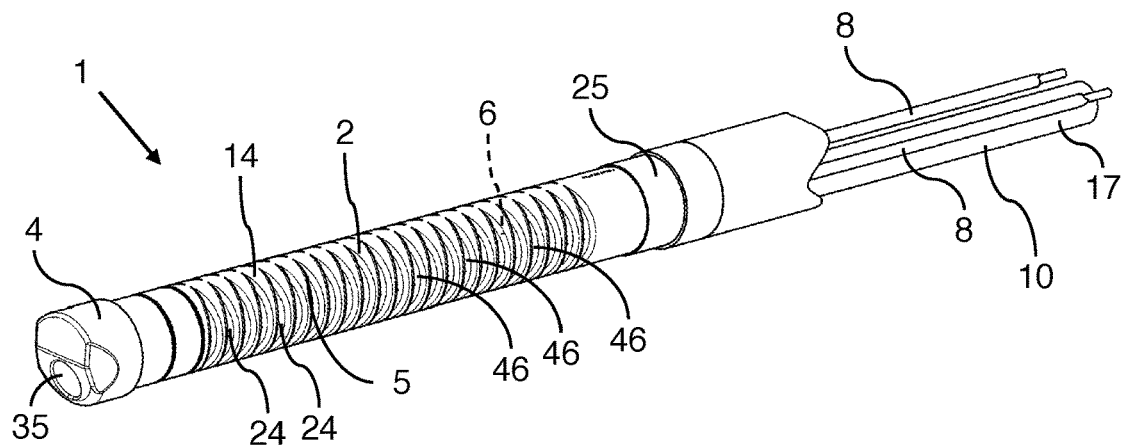
Figure 22:
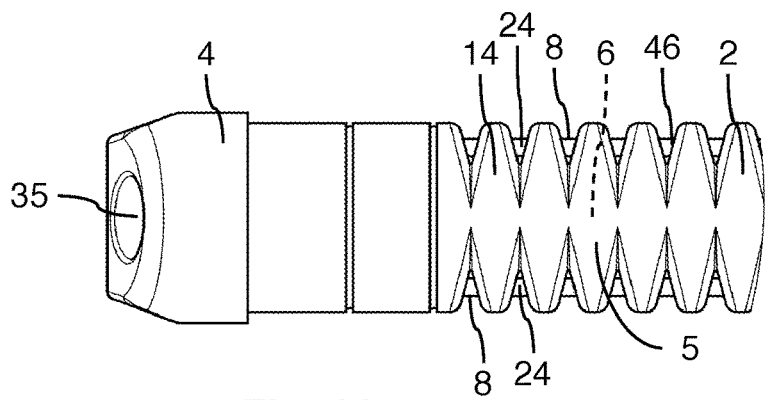
Figure 23:
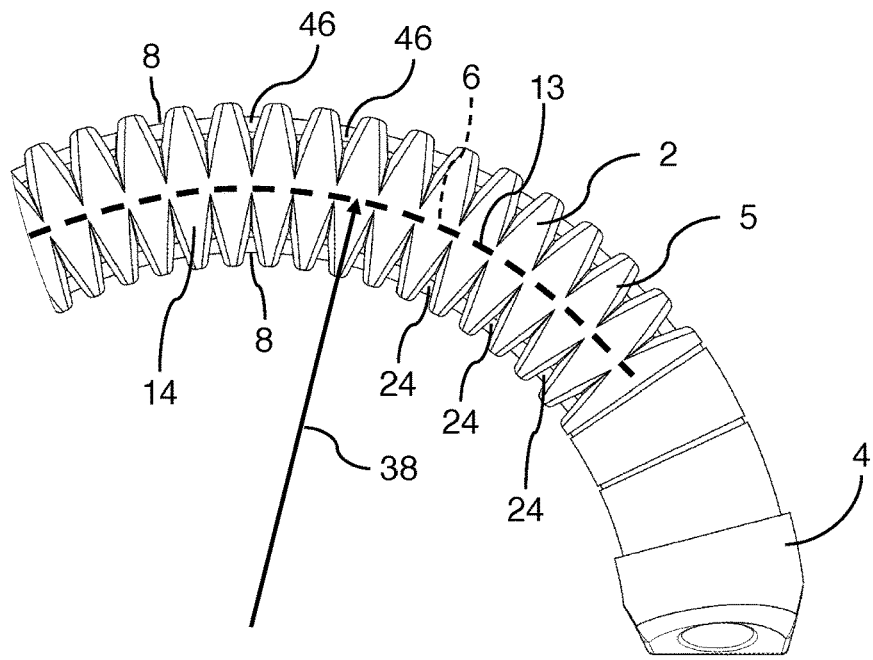
Figure 24:
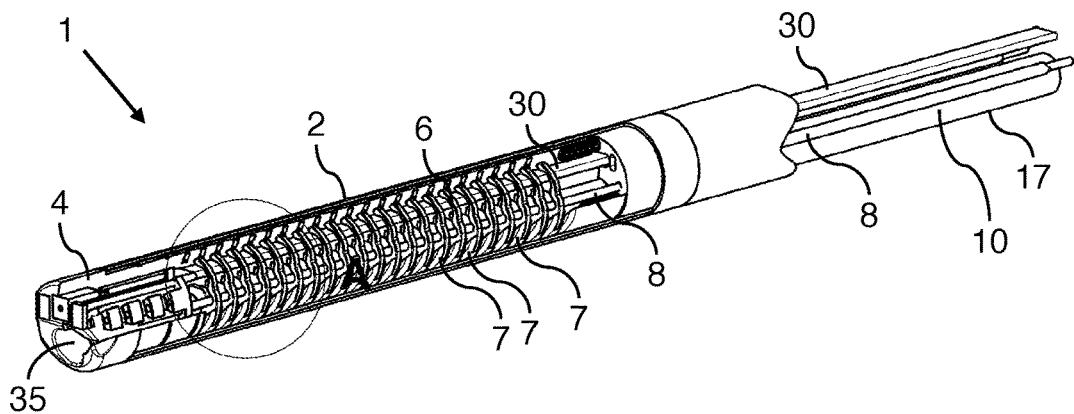
Figure 25:
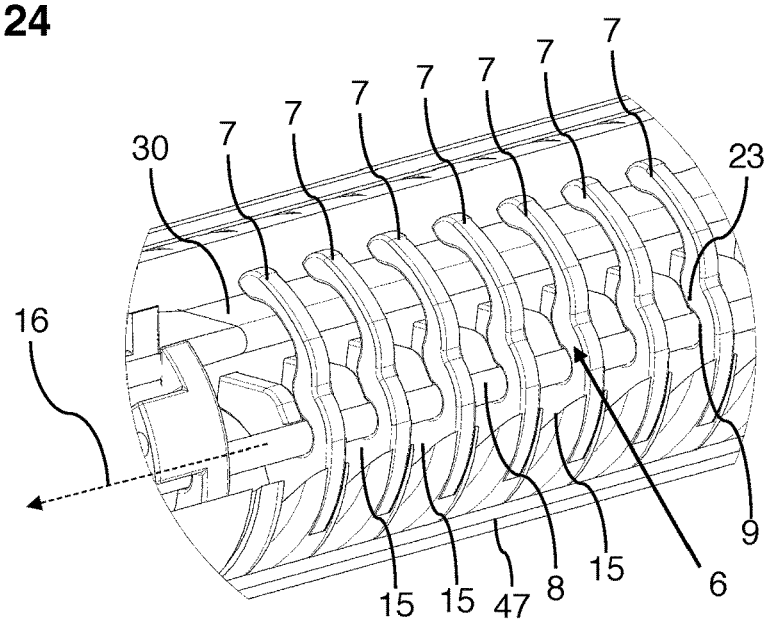
Figure 26:
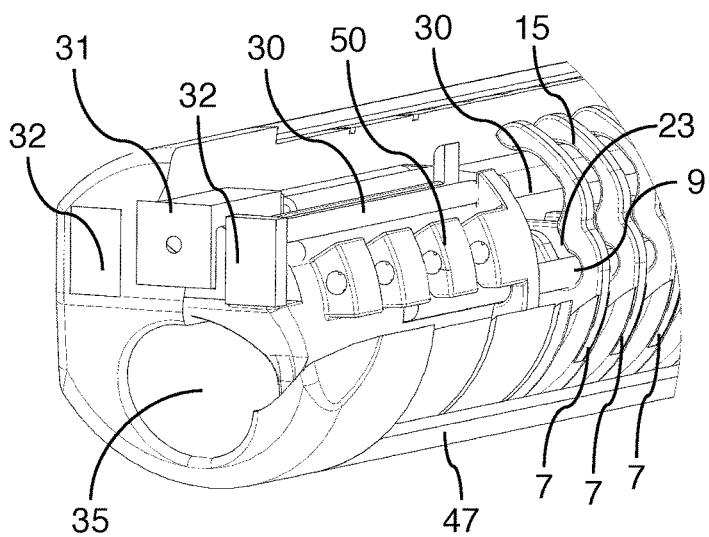
Figure 27:
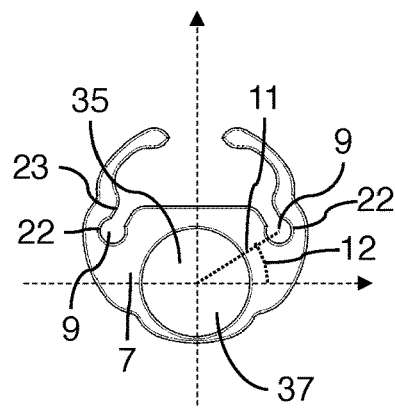
Figure 28:
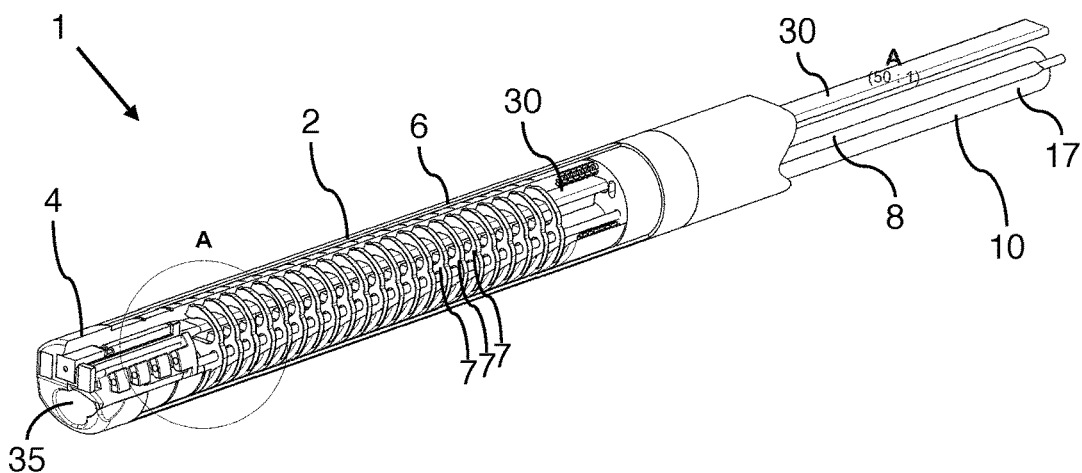
Figure 29:
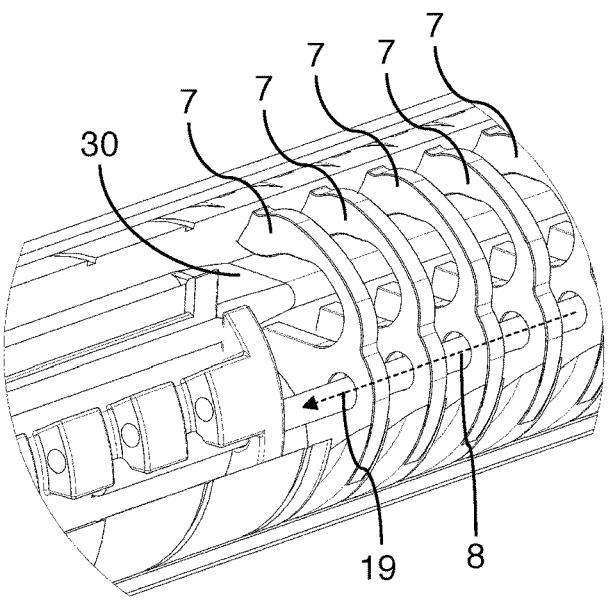
Figure 30:
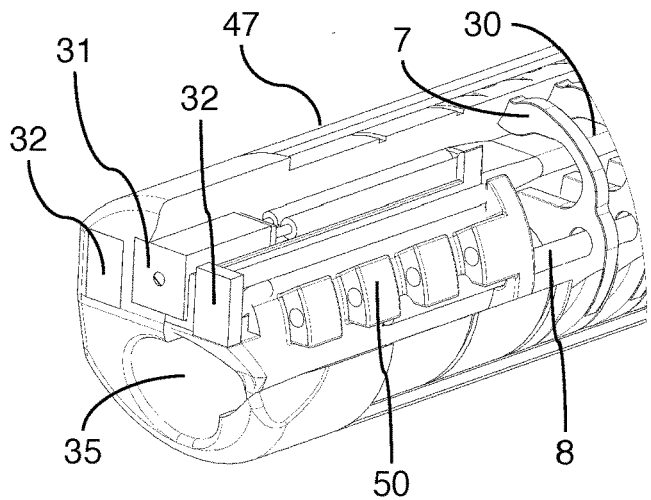
Figure 31:
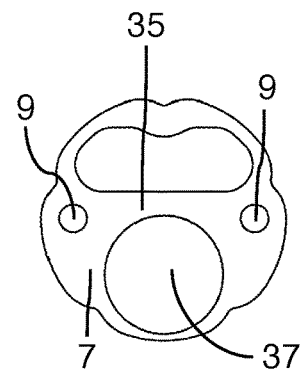

The flexible section 2 has a plurality of at least partially circumferential indentations 46, which are formed by casting/injection molding the investment composition 14, wherein the indentations 46 follow circular paths or helical lines. As shown in FIGS. 21 to 23, for example, the indentations can also run in a straight line, in particular perpendicular to a central axis. A suitable cross-sectional shape of the indentations is, for example, the V-shape that is discernible in FIGS. 21 to 23. FIGS. 1 to 45 and 50 to 59 show exemplary embodiments with two tension cords 8, 8a, 8b.

Figure 46:
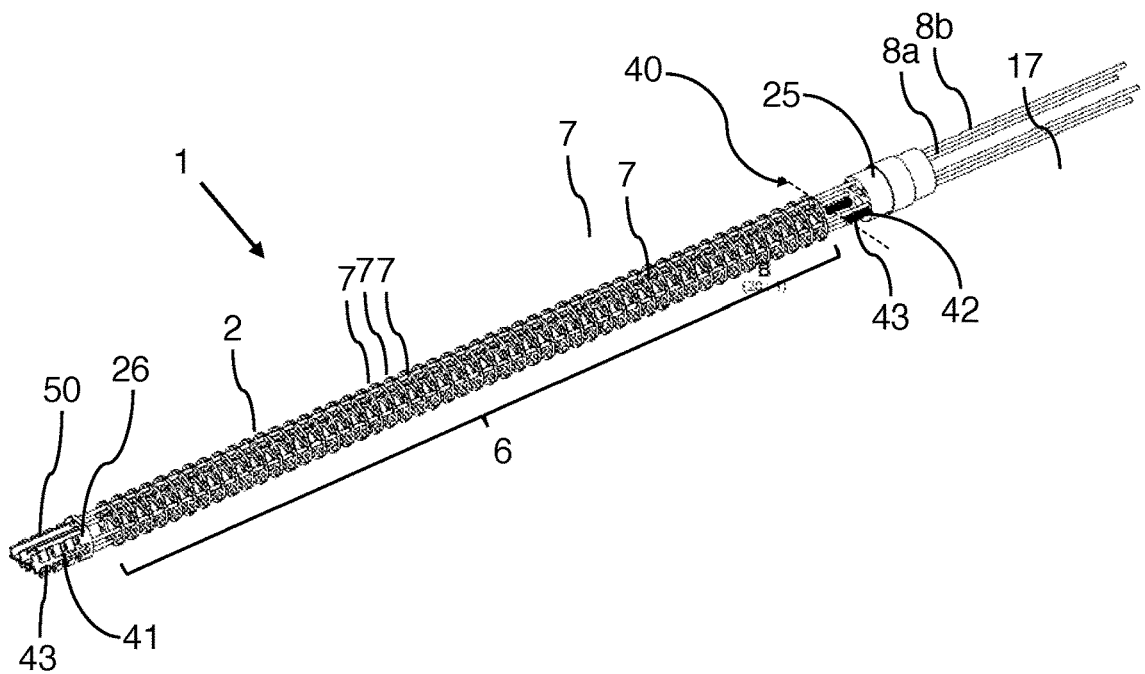
Figure 47:
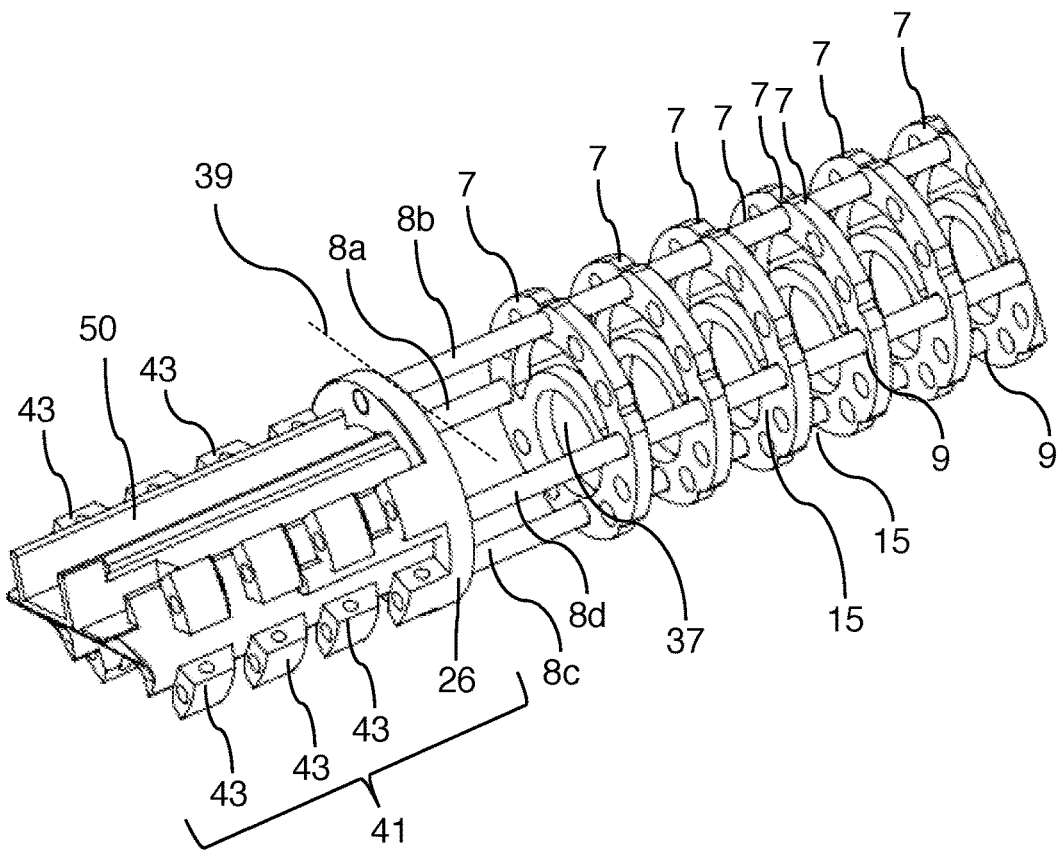
Figure 48:
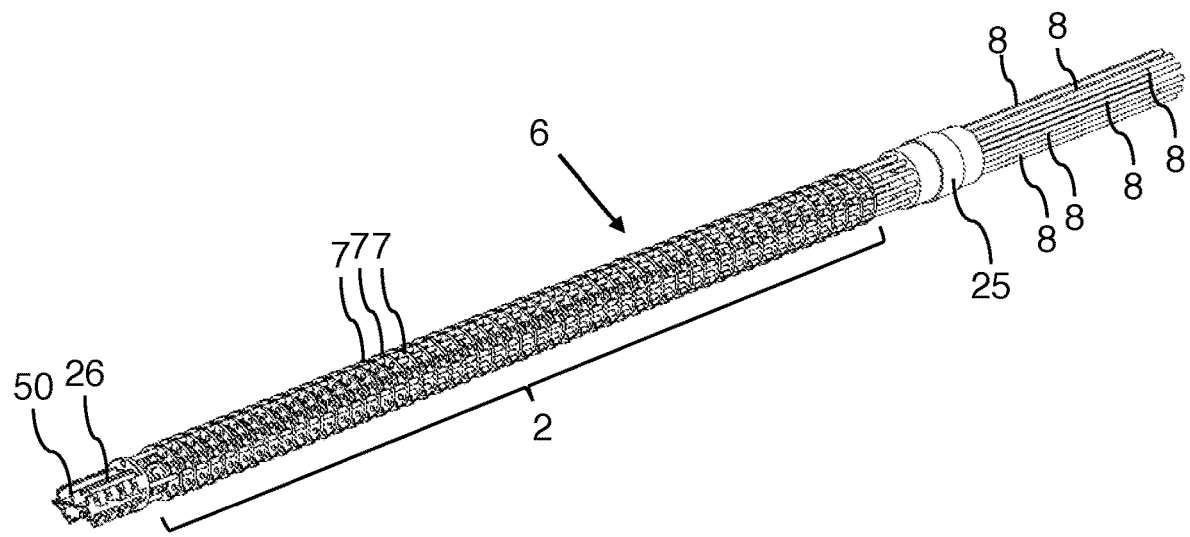
Figure 49:
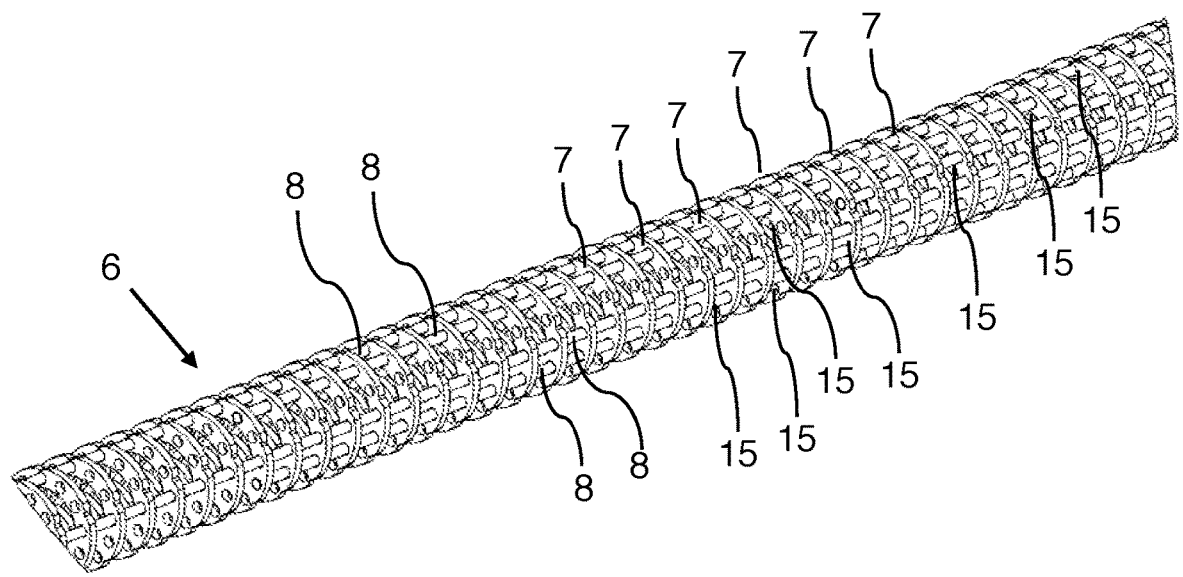
Figure 50:
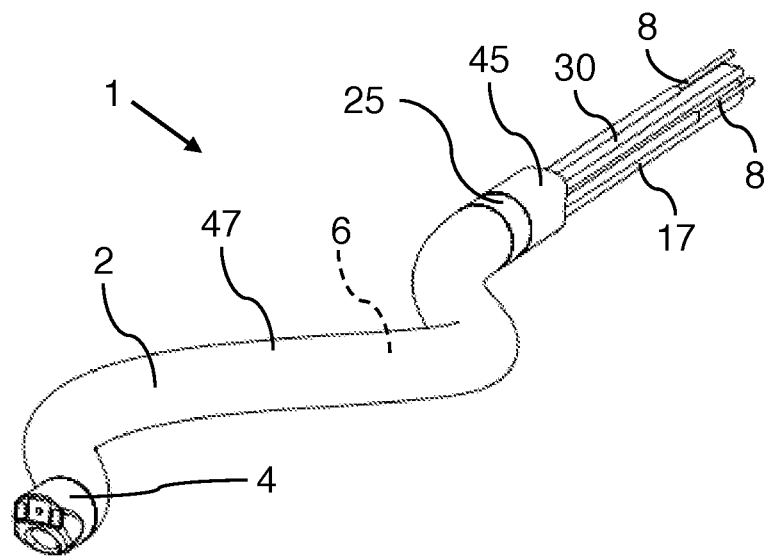
Figure 51:
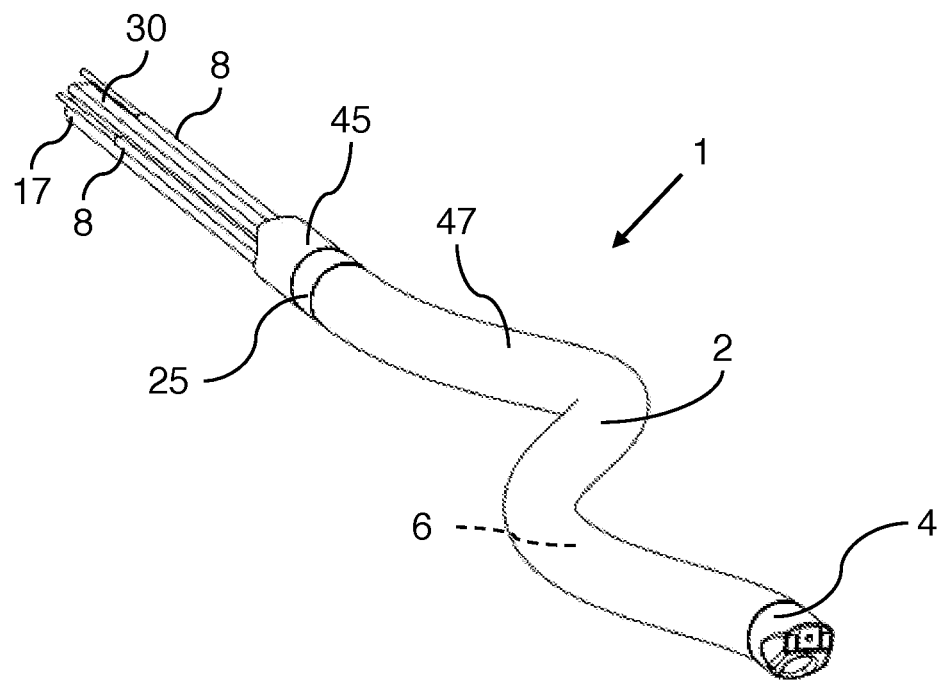

FIGS. 46, 47 show an exemplary embodiment with four tension cords 8a, 8b, 8c, 8d, and FIGS. 48 and 49 show an embodiment example with a large number of tension cords 8.

In FIGS. 48 and 49, it can be provided that the tension cords 8 do not all begin or end at the same axial height, for example for a control with multiple different or opposing successive curvatures.

Each of the guide elements guides all existing tension cords 8, 8a, 8b, 8c, 8d, wherein the tension cords 8, 8a, 8b, 8c, 8d are each connected to the distal tip segment 4 of the endoscope 1 and to individual guide elements 7 in a tension-resistant manner.

A possible production or assembly of a flexible endoscope 1 is described below.

For this purpose, a large number of guide elements 7 for guiding at least one tension cord 8 of the endoscope 1 are lined up in order to form a skeleton 6, even before the skeleton 6 is invested into an investment composition 14.

The guide elements 7 are aligned and held in position during investment in the investment composition 14 by an investment mold that is used for this purpose. Before the skeleton 6 is invested in the investment composition 14, each tension cord 8, 8a, 8b, 8c, 8d is introduced into tension guides 9 of the guide elements 7 along a longitudinal axis 16 of the endoscope 1. Alternatively, it is also possible to insert each tension cord 8, 8a, 8b, 8c, 8d laterally in tension guides 9 of the guide elements 7 transversely to a longitudinal axis 16 of the endoscope 1.

There, it is held in position by means of holding devices 23 formed on the guide elements 7.

The tension cords 8, 8a, 8b, 8c, 8d are then each invested in an inserted position of the investment composition 14.

The guide elements 7 are thus lined up in order to form the skeleton 6 by being threaded onto tension cords 8, 8a, 8b, 8c or onto an axial support structure 10.

In FIGS. 12 to 17, a great variety of combinations are shown. For example, lighting and sensor components can be arranged as desired within an encapsulation material. Image sensors 31 can be used as sensors, for example, and/or sensors 34 for pH value, pressure, temperature, magnetic field and/or position in space, in each case with any required reference sensors.

The lighting can be realized, for example, by means of an LED 32, which is arranged either in the tip segment 4 or—if necessary, with lateral irradiation for homogeneous illumination—in the investment composition 14, for example in transparent silicone.

Optical fibers 33, for example glass and/or plastic fibers, can be present with proximal illumination by an LED or a laser—also multispectrally with several wavelengths, for example.

For the lighting, a nanostructure and/or microstructure and/or a recess for molding a lens can also be provided in a casting mold, in particular the casting mold for the skeleton 6. The latter can optimize the illumination and/or project a light grid—for example for structured light measurements or strip light topometry.

FIG. 23 shows an angled silicone volume with free-standing cables or tension cords 8, which are guided and stabilized by the guide elements 7 in the form of insert rings or ribs.

The silicone compound or investment composition 14 acts between the guide elements 7 as an intervertebral disc. The combination of incised edge structures realized by the casting mold, free-standing tension cords 8, and guide elements 7 enables the smallest possible angulation radii or bending radii 38.

In further exemplary embodiments, instead of or in addition to the proximal anchoring aids or interlocking structures 43, gouged anchoring or interlocking structures are also embodied on the tip segment 4, or at least distally so.

Figure 41:
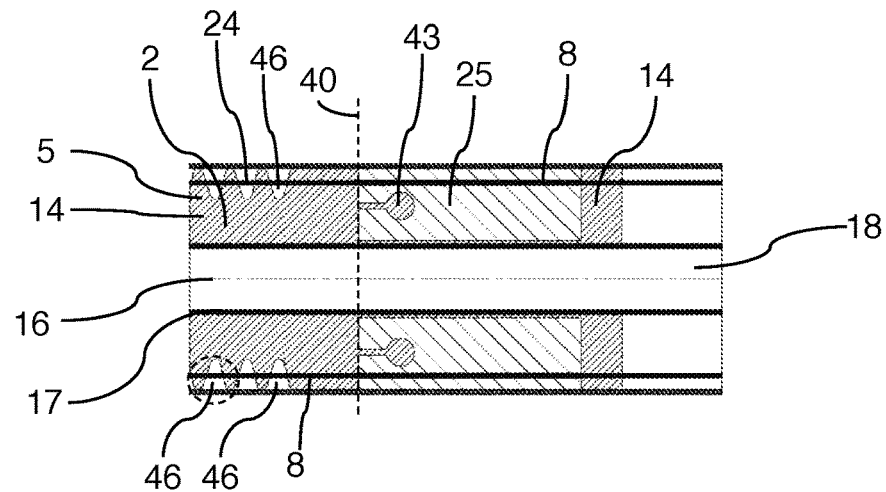
Figure 42:
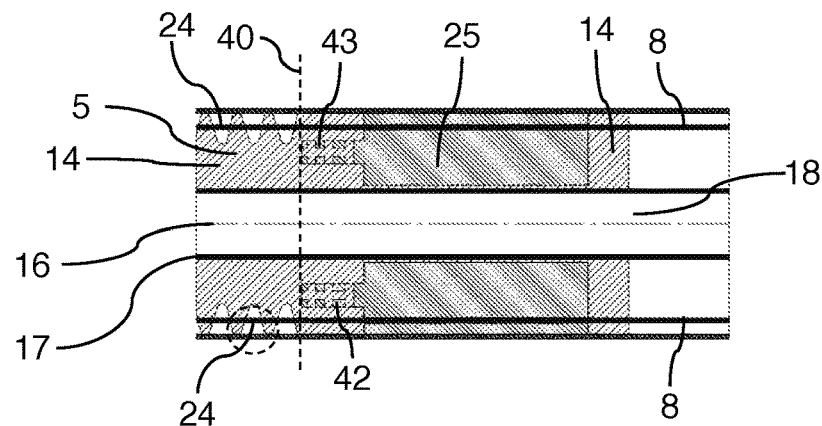
Figure 43:
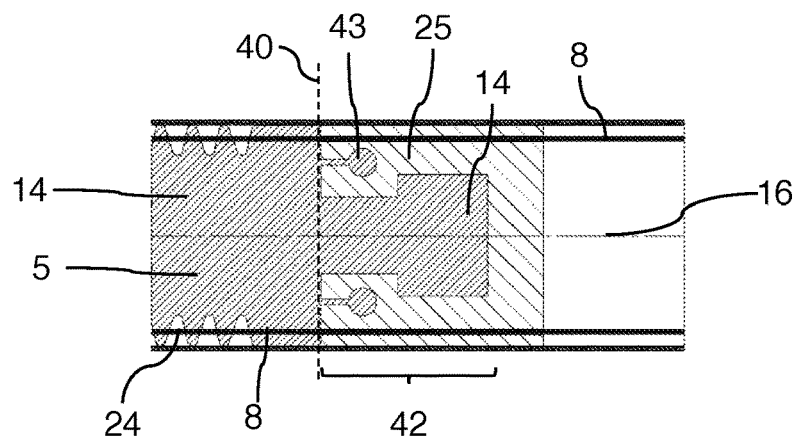

In FIGS. 41 to 43, for example, different gouges can be seen, into which the investment composition 14 can penetrate in order to anchor the flexible section 2.

Figure 52:
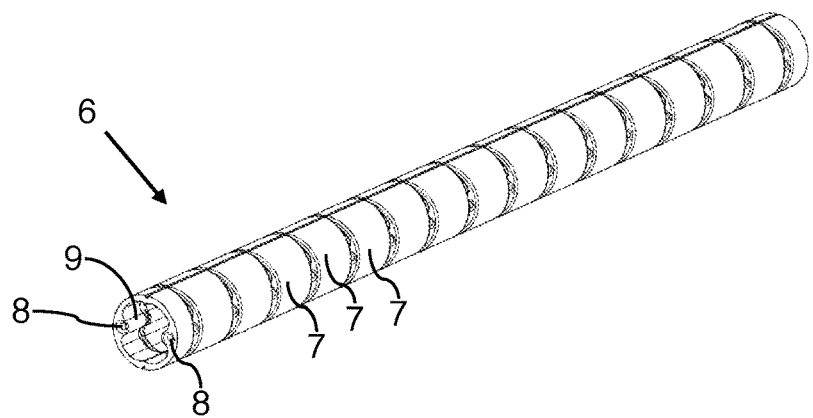
Figure 53:
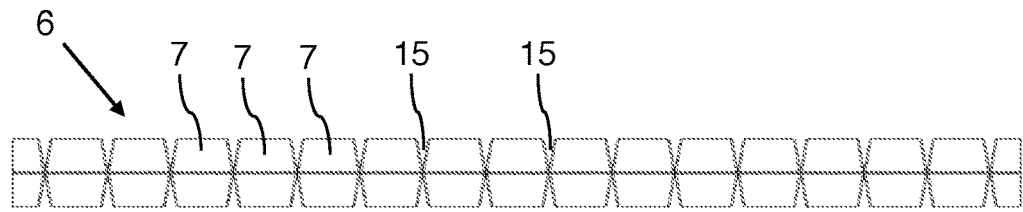

FIG. 52 shows an embodiment with a skeleton 6, which is designed as an exoskeleton.

FIGS. 56 to 59 show a variant in which the guide elements 7 are mounted on a tube structure, for example an elastomer, as individual segments, wherein the guide elements 7 do not touch each other but are held in position by gouges or grooves on the tube structure. These gouges or grooves thus form axial fixings 48 for the guide elements 7.

The interior of the tube structure can be used for the passing of lines and/or lighting fibers and/or for flushing or for tools/instruments.

The figures further show that the flexible section 2 is formed by means of an investment composition 14 and that the investment composition 14 is mechanically anchored in the tip segment 4 and a proximal counter bearing 25. The uncontrolled section of the endoscope 1, which is covered by a stabilization tube 45 or a flexible enveloping tube 47, adjoins the counter bearing 25 proximally.

Figure 44:
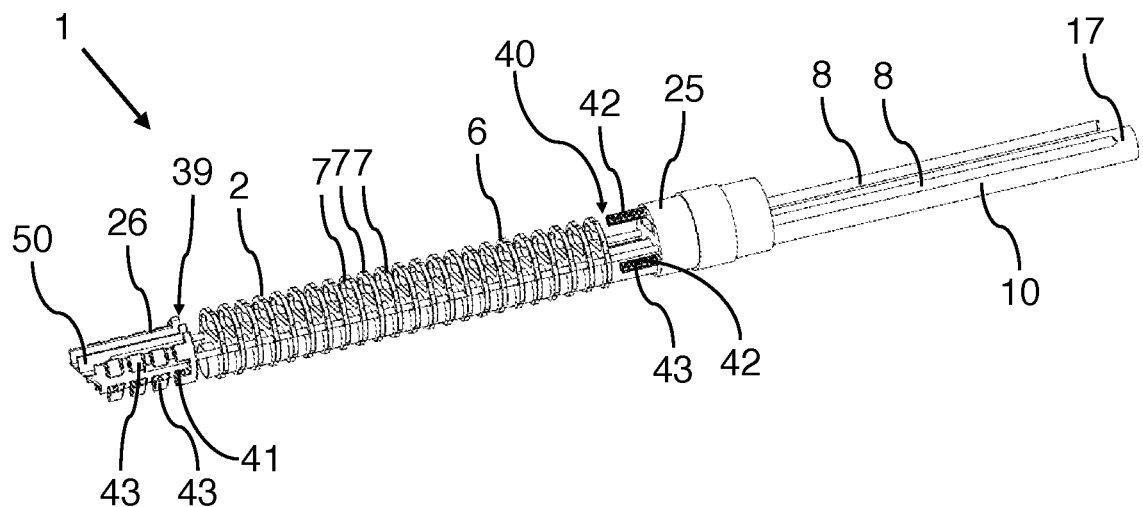
Figure 45:
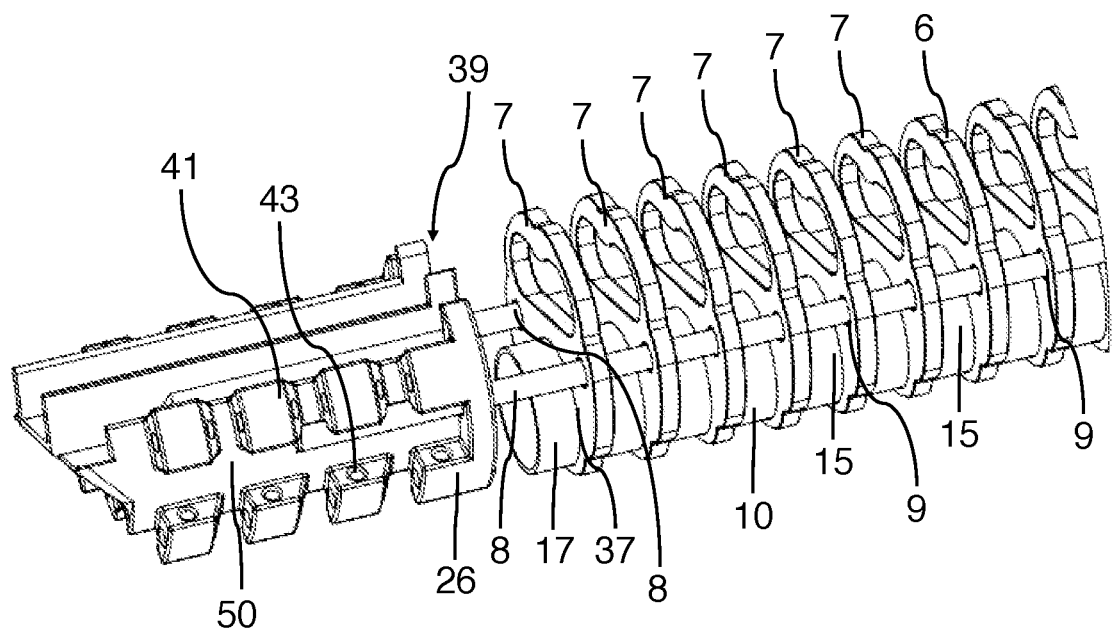

Here, the distal tip segment 4 forms a distal counter bearing 26. For this purpose, the tip segment can have a carrier body 50, for example an injection-molded one, as illustrated in FIGS. 44 and 45, which can form distal anchoring aids 41 for anchoring the investment composition 14 and can also carry optical or electronic components such as light sources or sensors. Furthermore, tension cords 8 can also be anchored in the carrier body 50. In addition to the carrier body 50, the distal tip segment can thus comprise electronic and/or optoelectronic components as well as parts of the investment composition 14. Because the distal counter bearing 26 is enclosed by the investment composition 14, it cannot be seen in FIGS. 1 to 6, 10, 11, and 21 to 23.

On the distal tip segment 4, more precisely on the carrier body 50, a proximal end surface 39 is also formed, upon which the flexible section 4 is supported.

The investment composition 14 extends distally beyond the proximal end surface 39. The investment composition 14 thus extends on both sides of the end surface 39.

In the same way, the proximal counter bearing 25 forms a distal end surface 40 upon which the flexible section 4 is supported with its other end.

The flexible section is thus clamped between the end surfaces 39, 40, wherein there exists a tensile stress due to the tension cords 8.

Here, too, the investment composition 14 extends proximally beyond the distal end surface 40 and thus extends on both sides of the end surface 40.

The tip segment 4, more precisely its carrier body 50, forms a distal anchoring aid 41 for anchoring the investment composition 14 in the distal tip segment 4.

The proximal counter bearing 25 also forms a proximal anchoring aid 42 for anchoring the investment composition 14 in the proximal counter bearing 25.

Both the distal anchoring aid 41 and the proximal anchoring aid 42 are implemented in different embodiments by means of a surface treatment and/or by means of an adhesion agent layer and/or by means of interlocking structures 43, such as depressions, gouges, transverse holes, or through-holes.

The distal tip segment 4 also has at least one electronic, in particular optoelectronic, functional element 44, for example a light source 32, 33, an image sensor 31, or some other sensor 34. Signal lines 30 can also be formed to and/or from the functional element 44.

The functional element(s) 44 is/are invested in the investment composition 14 and is/are thus fixed.

For this purpose, the investment composition 14 extends without interruption from the tip segment 4 into the flexible region 2.

The investment composition 14 is designed to be transparent or translucent. Thus, light can be received and/or emitted by the electronic functional element 44 through the investment composition 14.

At least one light source, preferably in the form of an LED 32, is invested in the investment composition 14 in the region of the tip segment 4 in such a way that the investment composition 14 serves as an optical fiber and optical diffuser for the light source.

The investment composition 14 invests an optical component, such as an optical fiber 33, in the region of the tip segment 4, or it forms such an optical component.

The investment composition 14 can, for example, form an optical beam-shaping element for shaping beams of illuminating light. The endoscope 1 can thus emit this illuminating light (if necessary, via illuminating optics 29), wherein the investment composition 14 is formed for this purpose by a micro/nanostructure in the region of the optical beam-shaping element.

The tension cords 8, 8a, 8b, 8c, 8d each have a coating that prevents the investment composition 14 from adhering or enables it to be torn away in a controlled manner when used for the first time.

Alternatively, a plating 49 can envelop each tension cord 8, 8a, 8b, 8c, 8d in the region of the flexible section 2 in order to prevent a direct contact of the at least one tension cord 8, 8a, 8b, 8c, 8d with structures outside of the plating 49.

The investment composition 14 is generally elastically deformable and—as mentioned above—transparent for at least one wavelength used for image capturing (possibly via image capturing optics 28) with the endoscope 1 and/or for a wavelength that is emitted as illuminating light by the endoscope.

In a method for producing or assembling one of the flexible endoscopes 1, a flexible section 2 of the endoscope 1 is formed together with a distal tip segment 4 of the endoscope 1 by means of an investment composition 14.

This is done in such a way that, after it has been introduced, the investment compound 14 extends from the flexible section 2 into the tip segment 4 and into a proximal counter bearing 25. The investment composition 14 thus structurally provides a tensile connection between the proximal counter bearing 25 and the distal counter bearing 26 in the tip segment 4.

In summary, it is thus proposed that, in the case of an endoscope 1 according to the invention, a skeleton 6 be formed in a flexible, controllable section 2 with guide elements 7 that are movable relative to one another, each of which guides at least one tension cord 8, 8a, 8b, 8c, 8d laterally.

What is claimed is:

1. A flexible endoscope for insertion into the human body comprising:
   a flexible section arranged in a distal end region of the endoscope;
   a tip segment distally adjoining the flexible section, said tip segment being controllable by means of at least one tension cord;
   wherein the flexible section has a skeleton, which has a plurality of guide elements and the at least one tension cord is guided by the guide elements; and
   wherein the guide elements of the skeleton are each formed in a disc-shaped manner and spaced apart from each other such that the guide elements do not contact each other and hence there is no direct transfer of forces between adjacent guide elements; and
   wherein the skeleton is invested into an investment composition which contributes to forming the flexible section; and
   wherein the investment composition is a polymeric material that is fully disposed in a space between adjacent guide elements such that the investment composition completely fills the space and thus is configured to support the guide elements against each other and transfer actuation forces from guide element to guide element.

2. The flexible endoscope according to claim 1, wherein respective tension guides of the guide elements each define a radial position and/or an angular position of the at least one tension cord in relation to a neutral fiber of the flexible section; and
   wherein the guide elements are lined up along the neutral fiber in regular intervals.

3. The flexible endoscope according to claim 1, wherein the skeleton is designed as an endoskeleton; and
   wherein an axial support structure for axially fixing the guide elements is formed along a longitudinal axis of the flexible section; and
   wherein the axial support structure is designed as a support tube with an internal working volume or as a flexible core.

4. The flexible endoscope according to claim 1, wherein the investment composition is at least one selected from the group of: injection-molded, and a two-component investment composition; and
   wherein an axial support structure is formed with the aid of a first component of the two-component investment composition, which is more rigid than a second component of the two-component investment composition.

5. The flexible endoscope according to claim 1, wherein the guide elements are each formed in a rigid manner and/or are aligned transversely to a running direction of the at least one tension cord transversely to a longitudinal axis of the endoscope; and
   wherein directly adjacent guide elements are each at most as far apart as their respective diameter.

6. The flexible endoscope according to claim 1, wherein the guide elements each support forces applied radially inwards and/or radially outwards from the at least one tension cord so that the at least one tension cord is prevented from cutting into the investment composition when the tip segment is actuated; and
   wherein the guide elements do not support a respective tension cord at least at a respective insertion point.

7. The flexible endoscope according to claim 1, wherein the guide elements each form passages for the at least one tension cord in which the at least one tension cord is insertable from the outside transversely to its respective running direction or along its running direction; and
   wherein the passages each comprise radially outwardly arranged support surfaces configured to support forces applied radially outwardly from the at least one tension cord 110.

8. The flexible endoscope according to claim 1, wherein the at least one tension cord is configured to be inserted transversely to a longitudinal axis of the endoscope into tension guides of the guide elements; and
   wherein the tension guides of the guide elements each form a holding device configured to prevent a respective tension cord from escaping from a respective tension guide; and
   wherein the holding device is formed by means of a clamping or crimping mechanism.

9. The flexible endoscope according to claim 1, wherein the at least one tension cord each comprise sections between the guide elements which are not covered by the investment composition so that friction losses between the at least one tension cord and the investment composition can be reduced when the tip segment is controlled.

10. The flexible endoscope according to claim 1, wherein the flexible section comprises a plurality of at least partially circumferential indentations, the indentations are formed by casting of the investment composition and/or wherein the indentations follow circular paths or helical lines.

11. The flexible endoscope according to claim 1, wherein at least two or at least four tension cords are formed; and
    wherein each of the guide elements guides at least one of the at least two tension cords or at least two of the at least four tension cords, and the tension cords are each connected to a distal counter bearing in the distal tip segment of the endoscope and/or to individual guide elements in a tension-resistant manner.

12. A method for producing or assembling a flexible endoscope comprising:
   lining up a plurality of guide elements for guiding at least one tension cord of the endoscope to form a skeleton before the skeleton is invested into an investment composition,
   wherein the guide elements are lined up such that they are spaced apart from each other and do not contact each other and such that respective spaces are formed between adjacent guide elements; and,
   wherein the investment composition is invested into the respective spaces between the guide elements forming the skeleton, such that the guide elements are supported against one another by the investment composition.

13. The method according to claim 12, wherein the guide elements are aligned and held in position during investment in the investment composition by an investment mold configured for this purpose.

14. The method according to claim 12, further comprising:
   inserting, before the skeleton is invested into the investment composition, the at least one tension cord along a longitudinal axis of the endoscope in tension guides of the guide elements; and/or
   inserting the at least one tension cord laterally transversely to the longitudinal axis of the endoscope in the tension guides of the guide elements; and
   wherein the at least one tension cord is held in position by means of holding devices formed on the guide elements so that the at least one tension cord is invested in an inserted position of the investment composition.

15. The method according to claim 12, wherein the guide elements are lined up to form the skeleton by means of threading of the guide elements onto tension cords of the at least one tension cord and/or onto an axial support structure.

16. The flexible endoscope according to claim 1, wherein the at least one tension cord is configured to be inserted transversely to a longitudinal axis of the endoscope into tension guides of the guide elements; and
   wherein the tension guides of the guide elements each form a holding device configured to prevent a respective tension cord from escaping from a respective tension guide; and wherein the guide elements are elastically or plastically deformable in a region of the tension guides in order to form the holding device; and
   wherein each holding device is formed by a clamping or crimping mechanism.

* * * * *